(12) United States Patent
Doherty et al.

(10) Patent No.: US 11,859,214 B1
(45) Date of Patent: Jan. 2, 2024

(54) AUTOMATED SYSTEM FOR SIMULATING THE HUMAN LOWER GASTROINTESTINAL TRACT

(71) Applicant: U.S. Government as Represented by the Secretary of the Army, Natick, MA (US)

(72) Inventors: Laurel A Doherty, Waltham, MA (US); Jason W Soares, Norfolk, MA (US); Steven Arcidiacono, Bellingham, MA (US); Sarah Pearce, Dedham, MA (US)

(73) Assignee: The Government of the United States, as represented by the Secretary of the Army, Washington, DC (US)

(*) Notice: Subject to any disclaimer, the term of this patent is extended or adjusted under 35 U.S.C. 154(b) by 1114 days.

(21) Appl. No.: 16/541,469

(22) Filed: Aug. 15, 2019

Related U.S. Application Data

(60) Provisional application No. 62/719,159, filed on Aug. 17, 2018.

(51) Int. Cl.
*C12M 1/00* (2006.01)
*C12M 3/06* (2006.01)
(Continued)

(52) U.S. Cl.
CPC .......... *C12N 5/0697* (2013.01); *C12M 21/08* (2013.01); *C12M 21/18* (2013.01); *C12M 23/58* (2013.01); *C12M 29/00* (2013.01); *C12M 41/18* (2013.01); *C12M 41/26* (2013.01); *C12M 41/48* (2013.01); *G01N 33/5088* (2013.01)

(58) Field of Classification Search
CPC ..... C12N 5/0697; C12M 21/08; C12M 21/18; C12M 23/58; C12M 29/00; C12M 41/18; C12M 41/26; C12M 41/48; G01N 33/5088
See application file for complete search history.

(56) References Cited

U.S. PATENT DOCUMENTS

| 5,525,305 A | 6/1996 | Minekus et al. |
| 8,703,479 B2 | 4/2014 | Marzorati et al. |

(Continued)

FOREIGN PATENT DOCUMENTS

| CA | 3013337 A1 | 8/2017 |
| CN | 101665758 A | 3/2010 |

(Continued)

OTHER PUBLICATIONS

Meddah et al. "The regulatory effects of whey retentate from Bifidobacteria fermented milk on the microbiota of the Simulator of the Human Intestinal Microbial Ecosystem (SHIME)", Journal of Applied Microbiology 2001, 91, 1110-1117.*

(Continued)

*Primary Examiner* — Liban M Hassan
(74) *Attorney, Agent, or Firm* — Kirsten Hiera

(57) ABSTRACT

An in vitro model of an in vivo gastrointestinal tract including an in vitro model of an in vivo small intestine including a plurality of fermentation vessels and an in vitro model of an in vivo large intestine including a plurality of fermentation vessels is provided. A method of simulating a biotransformation of food product through the human digestive tract using an in vitro model of an in vivo gastrointestinal tract is provided.

18 Claims, 18 Drawing Sheets

(51) Int. Cl.

| | | |
|---|---|---|
| C12N 5/071 | (2010.01) | |
| C12M 3/00 | (2006.01) | |
| C12M 1/40 | (2006.01) | |
| C12M 1/36 | (2006.01) | |
| C12M 1/34 | (2006.01) | |
| G01N 33/50 | (2006.01) | |
| C12M 1/02 | (2006.01) | |

(56) References Cited

U.S. PATENT DOCUMENTS

| | | |
|---|---|---|
| 9,540,676 B1 | 1/2017 | Zengler et al. |
| 9,938,558 B2 | 4/2018 | Embree |
| 2004/0101906 A1 | 5/2004 | Lacroix et al. |
| 2012/0058551 A1 | 3/2012 | Marzorati et al. |
| 2015/0072413 A1* | 3/2015 | Zenhausern .......... C12M 29/04 156/291 |
| 2016/0143949 A1 | 5/2016 | Ingber et al. |
| 2017/0227525 A1 | 8/2017 | Griffith et al. |
| 2018/0177831 A9 | 6/2018 | Borody |
| 2018/0230417 A1 | 8/2018 | Kerns et al. |
| 2018/0272346 A1 | 9/2018 | Griffith et al. |

FOREIGN PATENT DOCUMENTS

| | | |
|---|---|---|
| CN | 101113408 B | 5/2010 |
| CN | 102399692 B | 6/2013 |
| CN | 104107194 A | 10/2014 |
| WO | 2010/118857 A3 | 10/2010 |
| WO | 2017/065595 A2 | 4/2017 |
| WO | 2017/065595 A3 | 7/2017 |
| WO | 2017/134240 A1 | 8/2017 |
| WO | 2018/052953 A1 | 3/2018 |

OTHER PUBLICATIONS

Jalili-Firoozinezhad, Sasan, et al., "Complex human gut microbiome cultured in anaerobic human intestine chips", Sep. 2018, pp. 1-36.

Chen, Yanil, "Development and application of co-culture for ethanol production by co-fermentation of glucose and xylose: a systematic review", J Ind Microbiol Biotechnol., vol. 38, Issue 05, May 2011, pp. 581-597.

Molly, K., et al., "Development of a 5-step multi-chamber reactor as a simulation of the human intestinal microbial ecosystem", Applied Microbiology and Biotechnology, 1993, vol. 39, Issue 2, May 1993, pp. 254-258.

Kasendra, Magdalena, et al., "Development of a primary human Small Intestine-on-a-Chip using biopsy-derived organoids", Scientific Reports 8, Jan. 29, 2018, pp. 1-14.

Tzounis, Xenofon, et al., "Flavanol monomer-induced changes to the human faecal microflora", British Journal of Nutrition, vol. 99, Issue 04, Apr. 2008, pp. 782-792.

Minekus, Mans, et al., "A multicompartmental dynamic computer-controlled model simulating the stomach and small intestine. ATLA Altern Lab Anim", Alternatives to laboratory animals, vol. 23, Jan. 1999, pp. 197-209.

Guerra, Aurelie, et al., "Relevance and challenges in modeling human gastric and small intestinal digestion", Trends in Biotechnology, vol. 30, No. 11, Nov. 2012, pp. 591-600.

Tourlousse, Dieter M., et al. "Synthetic spike-in standards for high-throughput 16S rRNA gene amplicon sequencing", Nucleic Acids Research Advance Access, vol. 45, No. 04, Feb. 28, 2017, pp. 1-14.

MacFarlane, G. T., et al., "Validation of a Three-Stage Compound Continuous Culture System for Investigating the Effect of Retention Time on the Ecology and Metabolism of Bacteria in the Human Colon", Microbial Ecology, Mar. 1998, vol. 35, Issue 2, pp. 180-187.

Molley, K., et al., "Validation of the Simulator of the Human Intestinal Microbial Ecosystem (SHIME) Reactor Using Microorganism-associated Activities", Microbial Ecology In Health And Disease, vol. 07, Issue 04, 1994, pp. 191-200.

Kaur, A., et al., "Antioxidants in fruits and vegetables—the millennium's health", J. Food Sci., vol. 76, 2011, pp. H137-H1142.

Payne, AN et al. (2012) FEMS Microbiol Ecol 80:608-23.

Aghababaie et al. J Fod Eng (2015) 166:72-79.

* cited by examiner

Small intestine:

| Stage | Dynamic batch | Equilibration | Challenge | Recovery |
|---|---|---|---|---|
| Duration | 12-24 hours | 1 week | 1-2 weeks | 1-2 weeks |
| Purpose | Enable bacterial colonization | Establish a stable microbial community | Introduce dietary input and track changes | Monitor return to baseline conditions |
| Sampling capacity | Periodic sampling for quality control of stable community | | Experimental sampling of each domain throughout Challenge and Recovery stages | |

*Effluent from small intestine added to ascending colon vessel during challenge and recovery phases*

Large intestine:

| Stage | Dynamic batch | Equilibration | Challenge | Recovery |
|---|---|---|---|---|
| Duration | 12-24 hours | 2-3 weeks | 1-2 weeks | 1-2 weeks |
| Purpose | Enable bacterial colonization prior to vessel-to-vessel transfer | Establish a stable microbial community | Introduce dietary input and track changes | Monitor return to baseline conditions |
| Sampling capacity | Periodic sampling for quality control of stable community | | Experimental sampling of each domain throughout Challenge and Recovery stages | |

FIG. 2B

|  | Duodenum | Jejunum | Ileum | Ascending colon | Transverse colon | Descending colon |
|---|---|---|---|---|---|---|
| Temperature | 37°C | 37°C | 37°C | 37°C | 37°C | 37°C |
| Volume | 100-200 mL | 150-400 mL | 200-600 mL | 300 mL | 450 mL | 450 mL |
| Residence time | 0.5 hours | 2.5 hours | 4 hours | 12 hours | 18 hours | 18 hours |
| pH | 2.0-6.5 | 6.5-6.8 | 7.0-7.2 | 5.5±0.1 | 6.2±0.1 | 6.8±0.1 |
| Oxygen | 5% | 3% | 1.5% | 0% | 0% | 0% |

FIG. 2C

| | |
|---|---|
| Gas composition | Anaerobic atmosphere maintained using high-purity nitrogen |
| Agitation | Constant agitation to ensure evenly-distributed microbial community and prevent substrate settling |
| pH control | Domain-specific – pH maintained at 5.5 (ascending) 6.2 (transverse) and 6.8 (descending) by addition of HCl and NaOH. |
| Volume | Domain-specific – maintained by level sensors and incorporated high-capacity pumps; primary driver of residence time in continuous mode |
| Residence time | Incorporated high-capacity pumps facilitate vessel-to-vessel transfer and maintain domain-dependent turnover rate |
| Nutrient availability | Fresh media provided to ascending domain at constant rate; successively lower nutrient availability within transverse and descending domains |

FIG. 2D

| DYNAMIC BATCH MODE | CONTINUOUS MODE |
|---|---|
| Mimic colonic domains in separate vessels | Mimic colonic domains with sequential transition along large intestine |
| 24-48 hour fermentation, no media supplementation | 3-5 week fermentation with media supplementation to first domain |
| Domain-specific residence time not simulated | Domain-specific residence time simulated using vessel-to-vessel transfer |
| Level-sensor for real-time volume control | 1 input analyzed/run at multiple dosing/feeding points |

FIG. 2E

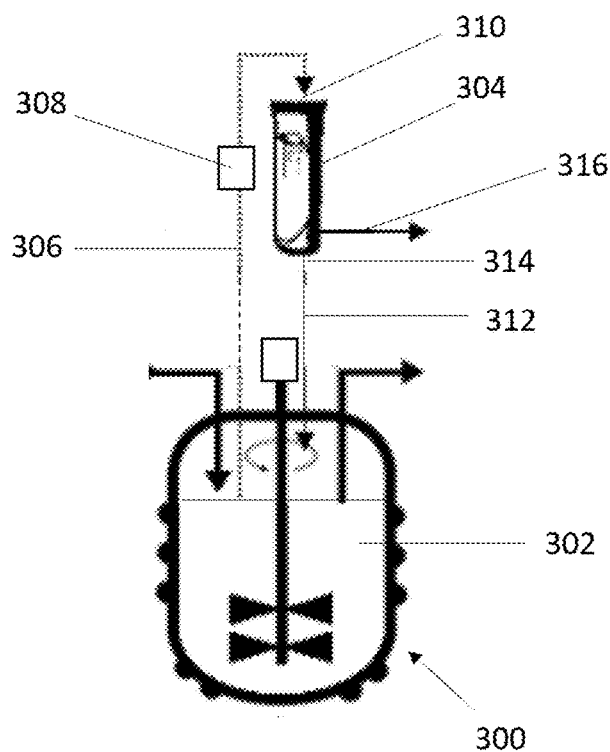

FIG. 2F

Monoculture: Escherichia coli Nissle 1917 (GFP) (EcNGFP)
Pairwise: EcNGFP + Bacteroides thetaioataomicron (B. Theta)
3-way: EcNGFP + B theta + Lactobacillus acidophilus (La)
4 way: EcNGFP + B theta + La + Escherichia coli K12

AUTOMATED SYSTEM FOR SIMULATING THE HUMAN LOWER GASTROINTESTINAL TRACT

CROSS-REFERENCE TO RELATED APPLICATIONS

This application claims priority to and the benefit of U.S. Provisional Patent Application Ser. No. 62/719,159 filed Aug. 17, 2018, the disclosure of which is incorporated herein by reference in its entirety.

STATEMENT OF GOVERNMENT INTEREST

The invention described herein may be manufactured and used by or for the U.S. Government for governmental purposes without the payment of any royalties thereon or therefor.

FIELD

This disclosure relates to a reactor system comprising an in vitro model of an in vivo digestive tract, methods of manufacture and use and components thereof.

BACKGROUND

Soldiers have had significant challenges with their gastrointestinal (GI) tract (the small intestine (aka small bowel) and the large intestine (aka the colon)) after deployment in foreign theaters usually resulting in lost duty time and reduced performance in the short term and often, longer term chronic issues later in deployment and after leaving active duty. The present disclosure relates to an apparatus that creates an important testing capability to help characterize the challenges the Soldiers face in terms of disruption of the microbial flora in their intestine, often termed gut microbiome, and a tool and method to evaluate a range of interventions that will help expedite/eliminate the GI health and performance issues they face.

One of the most commonly used complex systems, the Simulated Human Intestinal Microbial Ecosystem (SHIME), consists of five sequential chambers incorporating enzymatic digestion processes in single-stage stomach and small intestine chambers and microbial fermentation within three large intestine chambers inoculated by fecal-derived complex communities; however, the system does not account for small intestine microbiota or interactions between microbial and host epithelial cells. The SHIME system is centered on exposing dietary inputs to the range of pH conditions found in the small and large bowel sections while mimicking relevant transit times and extent of exposure to digestive enzymes and bile acids. The SHIME system also incorporates mucin-loaded beads to simulate host:bacteria interactions and explore mucolytic bacteria. However, the beads are pre-filled with commercially-purchased mucin that limits physiological relevance. A few models have attempted to mimic the peristaltic mixing of chyme in the small and large bowel including the most complex models to date, the TNO Intestinal Models TIM-1 and TIM-2. TIM-1 is an in vitro representation of the small bowel and incorporates not only peristaltic mixing but also hollow-fiber ultrafiltration to mimic nutrient absorption; TIM-2 incorporates these processes to simulate the proximal large intestine and includes a fecal-derived complex community. SHIME and the TNO Intestinal Models have been used to investigate the survivability of probiotic organisms and other beneficial inputs to study influence on gut health and support clinical studies. Although in vitro gastrointestinal models, have gained widespread acceptance due to a lack of feasible in vivo options particularly for the small bowel, they exhibit several limitations that mitigate in vivo relevance.

It is not currently possible to simulate host responses and feedback mechanisms, such as hormonal and neural control, or the host immune system within the current state-of-the-art of in vitro settings. In addition, current models lack a resident microbial community for the small intestine and are reliant on human fecal samples to seed the large intestine. 3D co-culture microfluidic models offer an alternative to the SHIME and TNO systems, however, these models are not anaerobic and cannot support metabolically-active bacteria within a full complex microbial community due to the density of cells and the need for insoluble media components; bacterial cells are just placed within the systems and are typically either mono or co-cultured only.

It would be advantageous to have an in vitro fermentation model that enables cost-effective screening of nutritional candidates for transition to exploratory food products for microbiome supplementation and modulation. It would also be advantageous to incorporate a mammalian cell organoid to actively create a supported mucosal layer, generated in real-time, from animal or human cells to simulate host:microbiome interface. The value of in vitro models can extend beyond nutrition with active work being done on xenobiotic exposure, drug bioavailability/impact/fate, pathogen attenuation and engineered sense/respond bacteria.

SUMMARY

In one embodiment, an in vitro model of an in vivo gastrointestinal tract is provided. The in vitro model of an in vivo gastrointestinal tract includes an in vitro model of an in vivo small intestine including a plurality of fermentation vessels and includes an in vitro duodenum model including at least one fermentation vessel having bile acids, sodium bicarbonate and duodenal enzymes disposed therein; an in vitro jejunum model including at least one fermentation vessel having jejunum diluent, growth medium and a complex or simplified mock community of a mixture of aerobic and aerotolerant microorganisms disposed therein; and an in vitro ileum model including at least one fermentation vessel having ileum diluent, growth medium and a complex or simplified mock community of a mixture of aerobic and anaerobic microorganisms disposed therein. The in vivo model also includes an in vitro model of an in vivo large intestine including a plurality of fermentation vessels and includes an in vitro ascending portion model including at least one fermentation vessel having growth medium and a complex or simplified mock community of anerobic microorganisms disposed therein at a pH of about 5.5; an in vitro transverse portion model including at least one fermentation vessel having growth medium and a complex or simplified mock community of anerobic microorganisms disposed therein at a pH of about 6.2; and an in vitro descending portion model including at least one fermentation vessel having growth medium and a complex or simplified mock community of anerobic microorganisms disposed therein at a pH of about 6.8.

In another embodiment, an in vitro model of an in vivo gastrointestinal tract is provided. The in vitro model of an in vivo gastrointestinal tract includes an inlet for the introduction of a mixture of a food product and gastric effluent; an in vitro model of an in vivo small intestine including a plurality of fermentation vessels, an in vitro model of an in vivo large intestine including a plurality of fermentation vessels and a controller. The multistage in vitro model of an in vivo small intestine includes an in vitro duodenum model, an in vitro jejunum model and an in vitro ileum model. The in vitro duodenum model includes a first fermentation vessel in fluid communication with the inlet through a first fluid conduit configured to supply the mixture of a food product and gastric effluent into the first fermentation vessel and including a first agitator connected to a first motor configured to move the first agitator to mix contents of the first fermentation vessel, a source of bile acids in fluid communication with the first fermentation vessel through a second fluid conduit including a first pump configured to supply bile acids into the first fermentation vessel, a source of sodium bicarbonate in fluid communication with the first fermentation vessel through a third fluid conduit including a second pump configured to supply sodium bicarbonate into the first fermentation vessel, and a source of duodenal enzymes in fluid communication with the first fermentation vessel through a fourth fluid conduit including a third pump configured to supply duodenal enzymes into the first fermentation vessel. The in vitro jejunum model includes a second fermentation vessel in fluid communication with the first fermentation vessel through a fifth fluid conduit including a fourth pump configured to supply a portion of the contents of the first fermentation vessel to the second fermentation vessel, the second fermentation vessel including jejunum diluent, growth medium, and a complex or simplified mock community of aerobic and aerotolerant microorganisms disposed therein and a second agitator connected to a second motor configured to move the second agitator to mix contents of the second fermentation vessel, a first membrane unit including configured to extract nutrients from the contents of the second fermentation vessel that pass there through and include a first membrane unit inlet, a first membrane unit outlet and a first membrane unit exit port through which the extracted nutrients exit the first membrane unit, a sixth fluid conduit including a fifth pump connected between the second fermentation vessel and the first membrane unit inlet and configured to supply a portion of the contents of the second fermentation vessel to the first membrane unit, and a seventh fluid conduit connected between the first membrane unit outlet and the second fermentation vessel and configured to return the contents of the second fermentation vessel that are not extracted by the first membrane unit to the second fermentation vessel. The in vitro ileum model includes a third fermentation vessel in fluid communication with the second fermentation vessel through an eighth fluid conduit including a sixth pump configured to supply a portion of the contents of the second fermentation vessel to the third fermentation vessel, the third fermentation vessel including ileum diluent, growth medium and a complex or simplified mock community of aerobic and anaerobic microorganisms disposed therein and a third agitator connected to a third motor configured to move the third agitator to mix contents of the third fermentation vessel, a second membrane unit including configured to extract nutrients from the contents of the third fermentation vessel that pass there through and include a second membrane unit inlet, a second membrane unit outlet and a second membrane unit exit port through which the extracted nutrients exit the second membrane unit, a ninth fluid conduit including a seventh pump connected between the third fermentation vessel and the second membrane unit inlet and configured to supply a portion of the contents of the third fermentation vessel to the second membrane unit, and a tenth fluid conduit connected between the second membrane unit outlet and the third fermentation vessel and configured to return the contents of the third fermentation vessel that are not extracted by the second membrane unit to the third fermentation vessel. The in vitro model of an in vivo large intestine includes an in vitro ascending portion model, an in vitro transverse portion model and an in vitro descending portion model. The in vitro ascending portion model includes a fourth fermentation vessel in fluid communication with the third fermentation vessel through an eleventh fluid conduit including an eighth pump configured to supply a portion of the contents of the third fermentation vessel to the fourth fermentation vessel, the fourth fermentation vessel including growth medium and a complex or simplified mock community of anerobic microorganisms disposed therein at a pH of about 5.5 and a fourth agitator connected to a fourth motor configured to move the fourth agitator to mix contents of the fourth fermentation vessel. The in vitro transverse portion model including a fifth fermentation vessel in fluid communication with the fourth fermentation vessel through an twelfth fluid conduit including an ninth pump configured to supply a portion of the contents of the fourth fermentation vessel to the fifth fermentation vessel, the fifth fermentation vessel including growth medium and a complex or simplified mock community of anerobic microorganisms disposed therein at a pH of about 6.2 and a fifth agitator connected to a fifth motor configured to move the fifth agitator to mix contents of the fifth fermentation vessel. The in vitro descending portion model including sixth fermentation vessel in fluid communication with the fifth fermentation vessel through an thirteenth fluid conduit including a tenth pump configured to supply a portion of the contents of the fifth fermentation vessel to the sixth fermentation vessel, the sixth fermentation vessel including growth medium and a complex or simplified mock community of anerobic microorganisms disposed therein at a pH of about 6.8 and a sixth agitator connected to a sixth motor configured to move the sixth agitator to mix contents of the sixth fermentation vessel. The controller is configured to selectively at least one of start, stop and regulate the flow there through of each of the fourth pump, sixth pump, eighth pump, ninth pump and tenth pump and selectively at least one of start, stop and regulate the speed of each of the first motor, second motor, third motor, fourth motor, fifth motor and sixth motor.

In Another embodiment, a method of simulating a biotransformation of food product through the human digestive tract using an in vitro model of an in vivo gastrointestinal tract is provided. The in vitro model of an in vivo gastrointestinal tract includes an inlet for the introduction of a mixture of a food product and gastric effluent, an in vitro model of an in vivo small intestine, and an in vitro model of an in vivo large intestine. The in vitro model of an in vivo small intestine including a plurality of fermentation vessels, including an in vitro duodenum model, an in vitro jejunum model and an in vitro ileum model. The in vitro duodenum model includes at least one fermentation vessel having bile acids, sodium bicarbonate and duodenal enzyme disposed therein. The in vitro jejunum model including at least one fermentation vessel having jejunum diluent, growth medium and a complex or simplified mock community of aerobic and aerotolerant microorganisms disposed therein. The in vitro ileum model including at least one fermentation vessel having ileum diluent, growth medium and a complex or simplified mock community of aerobic and anaerobic microorganisms disposed therein. The in vitro model of an in vivo large intestine including a plurality of fermentation vessels, including an in vitro ascending portion model including at least one fermentation vessel having growth medium and a complex or simplified mock community of anaerobic microorganisms disposed therein at a pH of about 5.5; an in vitro transverse portion model including at least one fermentation vessel having growth medium and a complex or simplified mock community of anaerobic microorganisms disposed therein at a pH of about 6.2; and an in vitro descending portion model including at least one fermentation vessel having growth medium and a complex or simplified mock community of anaerobic microorganisms disposed therein at a pH of about 6.8. The method includes mixing the food product and gastric effluent to form a first mixture; adding the first mixture to the bile acids, sodium bicarbonate and duodenal enzyme in the at least one fermentation vessel of the in vitro duodenum model including to form a second mixture; adding a portion of the second mixture to the jejunum diluent, growth medium and complex or simplified mock community of aerobic and aerotolerant microorganisms in the at least one fermentation vessel of the in vitro jejunum model to form a third mixture; adding a portion of the third mixture to the ileum diluent, growth medium and complex or simplified mock community of aerobic and anaerobic microorganisms in the at least one fermentation vessel of the in vitro ileum model to form a fourth mixture; adding a portion of the fourth mixture to the growth medium and complex or simplified mock community of anaerobic microorganisms in the at least one fermentation vessel of the in vitro ascending portion model to form a fifth mixture; adding a portion of the fifth mixture to the growth medium and complex or simplified mock community of anaerobic microorganisms in the at least one fermentation vessel of the in vitro ascending portion model to form a sixth mixture; adding a portion of the sixth mixture to the growth medium and complex or simplified mock community of anaerobic microorganisms in the at least one fermentation vessel of the in vitro descending portion model to form a seventh mixture; and removing a portion of the seventh mixture from the at least one fermentation vessel of the in vitro descending portion model.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIGS. 2B-2E include parameters of the mode stages and timeline as well as experimental parameters for operational embodiments of the embodiment of FIG. 2A;

FIG. 2F is a schematic illustration of another embodiment of an in vitro model of an in vivo gastrointestinal tract of the present disclosure;

DETAILED DESCRIPTION

Figure 1A:
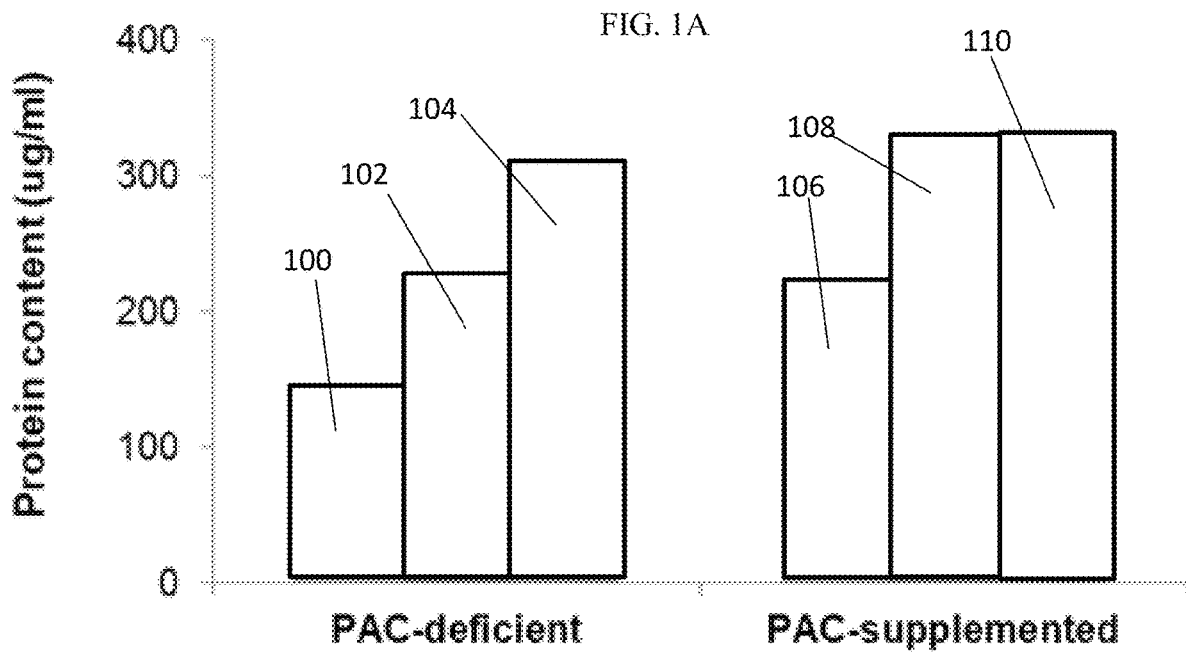
FIG. 1A is a graphic illustration of the results of conduct biotransformation studies of cranberry proanthocyanidins (PAC) as a function of colonic domain.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

Within the human large intestine, there are $10^{10}$-$10^{12}$ bacterial organisms with a ratio of 80-85% beneficial to 15-20% potentially harmful bacteria and ~70% of the body's immune cells.

Over last few years, there has been increasing scientific evidence that military-relevant stressors adversely influence gut microbiome community dynamics that are correlated with negative effects on host physiology including gut-brain axis, inflammation and immune function. Animal models are typically labor intensive, inefficient, cost ineffective and do not necessarily translate well to human responses. Human studies are ideal but may lack knowledge to inform study design, relying instead on literature to select parameters that may not be ideal; this knowledge gap can be addressed by using an in vitro model as an alternative starting point. The complexity of the gut microbiome processes is challenging, and physiologically relevant in vitro models are key to delineating the effects of stressors on gut microbes and exploring the functional community metabolism as opposed to just compositional changes. Since gut microbes are modulated by diet, nutrition is an avenue to build resiliency to stressor-induced microbiome changes; a fermentation model enables cost-effective screening of nutritional candidates for transition to exploratory food products for microbiome supplementation and modulation. The value of in vitro model extends beyond nutrition with active work being done on xenobiotic exposure, drug bioavailability/impact/fate, pathogen attenuation and engineered sense/respond bacteria.

The human small bowel is a complex and dynamic organ tasked with enzymatic digestion and absorption of nutrients. The role of nutrients and other beneficial compounds in support of Soldier health and performance is of great interest to the Army, specifically in relation to enhancing Human Performance through non-invasive nutritional strategies. However, detailed canvassing and characterization of nutrient digestion, bioavailability, and correlation to Soldier health is limited due to the small bowel's inaccessibility. Numerous in vitro models have been developed within academia toward overcoming this limitation, with varied levels of complexity ranging from single-stage digestive incubators to intricate computer-controlled systems emulating transit and passive absorption of nutritional components. However, inability to mimic more dynamic biological features within the small bowel limits the physiological relevance of the models. Notably, the small bowel microbiome is absent from current GI models. This microbial population is characterized by rapid conversion of simple carbohydrates to bioavailable sugars for the host as well as population fluctuations between fasted and fed states. The small bowel microbiome has generated increasing interest due to its contributions to host digestive processes and its potential role in gastrointestinal health and immunity. The purpose of the embodiments of the present disclosure, within the field of microbial ecology, is to develop a small bowel model with integrated resident microflora. The model of the present disclosure will, among other things, facilitate detailed understanding of the biotransformation and bioavailability of nutrients within the small bowel and study the needs of sustaining Soldier health and performance.

The overall objectives include 1) developing a novel fermentation model of the small bowel and the colon and 2) expanding the current knowledge of the fate of dietary inputs within the human gastrointestinal tract. The design and implementation of the small bowel model will leverage fermentation of a colonic (i.e. large intestine) fermentation model as part of a lower gastrointestinal tract model. As aspects of the present disclosure include a multi-stage model with distinct chambers for each domain of the small bowel. Other aspects of the present disclosure include a filtration system to emulate nutrient absorption processes. Single-component dietary compounds (e.g., maltodextrin, whey protein) can be used to assess model efficacy. The fermentation models of the small bowel and colon can be integrated to operate in tandem. This work will establish a novel capability and fill an important technological gap within the field of gut science, specifically digestion modelling.

The small bowel is comprised of three distinct sections. The proximal section, the duodenum, serves to neutralize chyme, the acidic mixture of partially-digested food and gastric juices. Pancreatic enzymes, a complex mixture of lipases, proteases, and amylases, are secreted into the chyme at this stage to facilitate digestion, as are bile acids, which serve to emulsify lipids in order to promote digestion by lipases. The jejunum and ileum comprise sections wherein the chyme is digested and nutrients absorbed, with the ileum emptying into the large intestine. The topography of the intestinal wall is comprised of complex structures such as circular folds and villi, creating an immense surface area for absorption, which is achieved through a combination of passive diffusion, facilitated diffusion, and active transport. Motility of the chyme is facilitated by peristaltic activity as well as hormonal and neural regulation. Although the upper portions of the gastrointestinal tract (GIT) were once assumed to be sterile environments, the entire length is now known to be colonized by diverse microbiota.

Other aspects of the present disclosure include an in vitro model of the small bowel that will mimic human physiology, to include enzymatic digestion processes, nutrient absorption, and microbial metabolism. Furthermore, the in vitro model will facilitate understanding of the complex biological processes that occur in the small bowel by taking advantage of the broad experimental capacity afforded by in vitro systems, relative to in vivo studies.

Being situated in the center of the GIT (gastrointestinal tract), the small bowel is relatively inaccessible for in vivo observation; therefore, in vitro models have long been employed as an alternative source of study. The simplest digestion models consist of one to two static vessels representing the stomach and small bowel. Dietary inputs (i.e. food products or model components) are first exposed to acidic conditions representative of gastric juice, followed by an extended incubation period (2-5 hours) under conditions to mimic the duodenum. For this latter stage, representative pancreatic enzymes and bile are added to mimic functional enzymatic digestive processes. Higher-fidelity digestion models incorporate these elements but with a full representation of the distinct sections of the small bowel. Substantially less is known regarding the small bowel commensal bacterial community compared to the large intestine (colonic) microbiome, but the small bowel is notably the first stage of the GIT where ingested nutrients and resident microflora interact. The microbial population of the small bowel also competes with the host for absorption of nutrients, so the host employs immune responses to maintain a stable microbial population. Overgrowth of small bowel bacteria has been linked to malabsorption and is associated with a variety of chronic gastrointestinal disorders. The small bowel microbiome role in digestion, human health, and disease is generating increasing interest and may be pivotal to understand for future efforts on enhancing Soldier gut and immune health.

Aspects of the present disclosure also include expanding fermentation capabilities to develop an in vitro fermentation model of the small bowel with resident microbiota. The relatively fast transit time of chyme through the small bowel precludes fermentation of complex carbohydrates, and temporal fluctuations in nutrient supply lead to high population and phylogenetic variability between fasted and fed states. Small bowel commensal microbiota specialize in rapid uptake and bioconversion of simple carbohydrates and soluble dietary components including sugars, lipids and other calorie-dense components. The microbial biotransformation processes can produce many of the beneficial fermentation byproducts, such as short-chain fatty acids (SCFAs) and amino acids, that are similarly derived from fermentation processes within the large intestine. The small bowel microbial community can conform to a gradient in response to changes in pH, nutrient availability, and presence of atmospheric oxygen over the length of the tract. The duodenum bacterial population is relatively sparse due to short transit time and exposure to acidic stomach effluent, digestive enzymes, and bile acids. The jejunum is somewhat more densely populated, but the majority of small bowel microbes are found in the ileum.

Aspects of the present disclosure include a small intestine and colonic models that utilize an automated (e.g., DASgip system) parallel bioreactor platform with a centralized computer for completely automated process control mimicking of all three portions of the small intestine and all three domains of the colon under distinct conditions. Use of the colonic model currently focuses on biotransformation of insoluble polyphenolic constituents, which survive transit through the upper GIT, to assess influence on colon and immune health in addition to exploring metabolic capacity of microbial community as a function of military-relevant stressors. The small bowel model will complement the colonic model program by expanding the ability to mimic the function of the human digestive system and enable a more accurate representation of the interplay between small and large intestine microbiomes. The small bowel model included herein can mimic the function and processes of the three sections of the small bowel and be developed in two phases: single-stage for baseline operation, and multi-stage for implementation. As part of our efforts, a representative domain-specific microbiome can be developed and used to enhance in vivo relevance to the extent feasible. A tangential-flow filtration system, modeled after the hollow-fiber ultrafiltration system can be used to mimic absorption of nutrients by the host. To evaluate the effectiveness of the filtration technique, samples from the filtrate and retentate can be subjected to proximate analysis (i.e. compositional analysis of proteins, amino acids, lipids, simple and complex carbohydrates, and vitamins and minerals). The multi-stage model can be designed and implemented, with each section of the small bowel represented in a single fermentation chamber and the central computer system enabling automated transport between chambers and addition of bile acids and pancreatic enzymes. All three chambers of the model can be seeded with the domain-specific microbial inoculum.

Other aspects of the present disclosure include a method to study the effects of dietary inputs to include small bowel fermentable and soluble substrates. Small bowel fermentation primarily comprises rapid transformation of less complex carbohydrates into simple sugars, as well as de novo production of amino acids and SCFAs from a range of soluble compounds, all of which can be readily absorbed by the host. Dietary inputs, either single-components representative of proteins, fiber, and other nutritional components, or more complex food products can be exposed to synthetic solutions mimicking gastric acid. The resultant chyme can then be introduced to the small bowel model configured as a multi-stage embodiment for generating detailed knowledge of digestive processes. Analytical techniques can be employed to investigate the effect of dietary inputs on small bowel microbial population (e.g., 16s rRNA), induced metabolic byproducts (e.g., short and branched chain fatty acids, SCFA/BCFA), and nutrient bioavailability, including the use of third party testing (e.g., proximate analysis). Effluent from the small bowel model can be utilized as a nutrient feed for the colonic model in order to investigate the effects of dietary inputs on the two microbiomes synergistically. Coupling of small and large intestine models in current systems (e.g., SHIME) has limited efficacy in part due to modeling limitations such as lack of resident microbiota in the small bowel portion and the inability to mimic nutrient absorption. Embodiments of the present disclosure enable more representative effluent to feed the colonic model resulting in an expanded capability to characterize biotransformation of dietary inputs and their effects on gut health.

Aspects of the present disclosure include a fermentation model of the small bowel. The model can include the three sections of the small bowel, emulate nutrient absorption through ultrafiltration, and incorporate resident microbiota in each section. The small bowel microbiome can include a single-stage baseline fermentation model, or a multi-stage model can be implemented using a representative microbiome to seed each distinct section of the small bowel. The multi-stage model can sequentially link the domains in order to mimic the digestive processes of the small bowel including simulating the function of the small bowel with the digestion and breakdown of simple dietary inputs in order to validate the utility of the model. This model will operate in tandem with the aforementioned colonic model to enable more complete understanding of biotransformation of dietary inputs through the human digestive tract to enhance strategies toward modulating gut microbiome to sustain/enhance Soldier health and performance.

Efficacy of digestion can be dependent on numerous variables including choice of food matrix, residence time, mixing, secretion rates of pancreatic enzymes and bile, pH, and absorption of nutrients. To emulate this dynamic process in vitro, embodiments of the present disclosure can include a commercial bioreactor platform, such as, for example, the DASgip automated parallel bioreactor. The DASgip system can employ, for example, a four-vessel fermentation platform with fermentation volumes in range of 200-1000 ml. Each vessel can contain two or more feed lines from peristaltic pumps that can be employed to introduce acid/base for pH control and enzyme/bile medium supplementation for continuous cultures. The system can include a temperature control module with a range of 20-60° C. and a stirring module with agitation rates from 50-1000 rpm. Each vessel can contain a pH probe for real-time assessment of culture pH and redox probe for real-time measurements of oxygen content. Inlet gas to control anaerobicity is facilitated through automated mass flow meters. Level sensors within each vessel enable volume control during fermentative processes. The DASgip control software allows vessel-specific process control, enabling concomitant analyses at varying anaerobicity, pH, mixing rate, feeds, etc. The control software can also coordinate actions in response to specific triggers (e.g., dispensing pancreatic juice in response to a change in pH or volume), which will impart an element of dynamic responsiveness and autonomy not present in most current models. Additional accessory pumps with a high capacity volume and large tubing size to minimize fouling and clogging of lines will be employed for vessel transfers during the multi-stage setup.

In comparison to the colon, the small bowel microbiome can exhibit a lower microbial population density and is subject to distinct fed and fasted states; for these reasons, the microbial population is thought to have high temporal variability. Phylogenetic sequencing of the small bowel microbiome is limited; however, ileostomy samples, coupled with samples from endoscopy, colonoscopy, and sudden death victims, have nonetheless elucidated an understanding of the in vivo role of the small bowel microbiome. There are marked similarities between duodenal/jejunal and oral microbiota, albeit limited to acid-tolerant strains, and suggests an oral route for initial colonization of the small bowel; the ileum contains a larger proportion of obligate anaerobes consistent with gut bacterial species. To simulate the small bowel microbiome in vitro, oral bacteria can be collected from human volunteers and pooled to normalize differences between individuals and subjected to acidic conditions emulating gastric juice to select for acid-tolerant strains. The oral bacteria can form the basis for the inoculum for the three vessels of the model; in addition, the ileum inoculum can be supplemented by a proportionate amount of fecal slurry. To assess the accuracy of the model microbiome, 16s rRNA sequencing can be performed and the results compared to characterizations in literature. Alternatively, a simplified mock community of 4-15 organisms can be developed using isolates with known characteristics to represent major phyla and functions of the in vivo small intestine microbiome.

The complexity of the gut microbiome processes is challenging, and physiologically relevant in vitro models are key to delineating the effects of stressors on gut microbes and exploring the functional community metabolism as opposed to just compositional changes. Since gut microbes are modulated by diet, nutrition is an avenue to build resiliency to stressor-induced microbiome changes that cause GI distress.

Aspects of the current disclosure can include incorporating a mammalian cell organoid to actively create a supported mucosal layer derived from animal or human cells to simulate host:microbiome interface and explore real-time mucolytic bacteria and host:microbiota responses, expanding the resident microbial environment to include that of the small intestine, and adding the option of a simplified microbial community in lieu of human clinical samples.

The small intestine model includes the three domains (duodenum, jejunum and ileum) with the following capabilities (see Table 1 for additional conditions); removal of nutrients commonly absorbed in vivo in a physiologically relevant manner; control over temperature, pH, volume and flow rate; and ferments a full range of microbial flora commonly found in vivo (both full complex consortia & simplified functional consortia for experimental purposes).

TABLE 1

Small bowel domain dependent conditions:

| | Duodenum | Jejunum | Ileum |
| --- | --- | --- | --- |
| Transit time[1] | 0.25 hrs | 2-3 hrs | 3-4 hrs |
| pH[2] | 5.4-7.5 | 5.3-8.1 | 7.0-7.5 |
| Oxygen partial pressure[2] | 32 torr | — | 11 torr |
| Microbe density[3] | $10^4$-$10^5$ CFU/mL | $10^5$-$10^7$ CFU/mL | $10^7$-$10^9$ CFU/mL |
| Predominant microbes[3,4] | Proteobacteria Lactobacillus Streptococcus Veillonella | Proteobacteria Lactobacillus Streptococcus Veillonella | Clostridium clusters Bacteroides Proteobacteria |
| References | (1) Gbassi, G. K., et al. *International Dairy Journal* (2011) 21:97-102 (2) Alminger, M., et al. *Comprehensive Reviews in Food Science and Food Safety* (2014) 13:413-36 (3) Booijink, C. CGM, et al. *Future Microbiology* (2007) 2: 285-95 (4) van den Bogert, B., et al. *FEMS Microbiology* (2013) 85: 376-88 | | |

Aspects of the disclosed embodiments are directed to a lower GI tract system that integrates models of both small and large intestine that include microbial flora fermenting at physiologically relevant conditions. The large intestine model simulates the three domains (ascending, transverse and descending) of the colon each with; control over temperature, pH, volume and flow rate; and capable of fermenting a full range of microbial flora (complex & simplified). A more comprehensive set of capabilities of the large intestine model is shown in Table 2.

TABLE 2

The large intestine model key attributes.

| KEY FEATURES | EXPERIMENTAL CAPACITY |
| --- | --- |
| Batch or Continuous | Mimic colonic domains including sequential transition along large intestine |

TABLE 2-continued

The large intestine model key attributes.

| KEY FEATURES | EXPERIMENTAL CAPACITY |
| --- | --- |
| 8 independently controlled vessels | Mimic domain-specific parameters (ph, residence time, etc.) |
| 200-1000 ml volume | Domain-specific kinetic-based sampling of all domains simultaneously |
| 4 feed lines/vessel for nutrient feed/pH control/colon emptying | 1 input analyzed/run at multiple dosing/feeding points |
| Level-sensor for real-time volume control | Stable, complex community on onset of nutritional/bacterial challenge |
| Real-time anaerobic/pH monitoring/control | Fasted/fed states cycling |
| High-capacity pumps for insoluble material transport | Total experimental window = 4 weeks |

An embodiment of the large intestinal model is implemented to explore domain-dependent biotransformation of nutritional inputs and microbial metabolism as a function of stress. FIG. 1A illustrates the capability to conduct biotransformation studies of nutritional inputs, specifically cranberry proanthocyanidins (PAC) in this example, as a function of colonic domain. In FIG. 1A, graph 100 represents the ascending portion (pH 5.5), graph 102 represents the transverse portion (pH 6.2), graph 104 represents the descending portion (pH 6.8) for PAC-deficient medium and graph 106 represents the ascending portion (pH 5.5), graph 108 represents the transverse portion (pH 6.2), graph 110 represents the descending portion (pH 6.8) for PAC supplemented medium. The domain-specific conditions elicit differential microbial metabolism and competition for PAC that generates domain-specific PAC metabolites with anti-inflammatory properties.

Figure 1B:
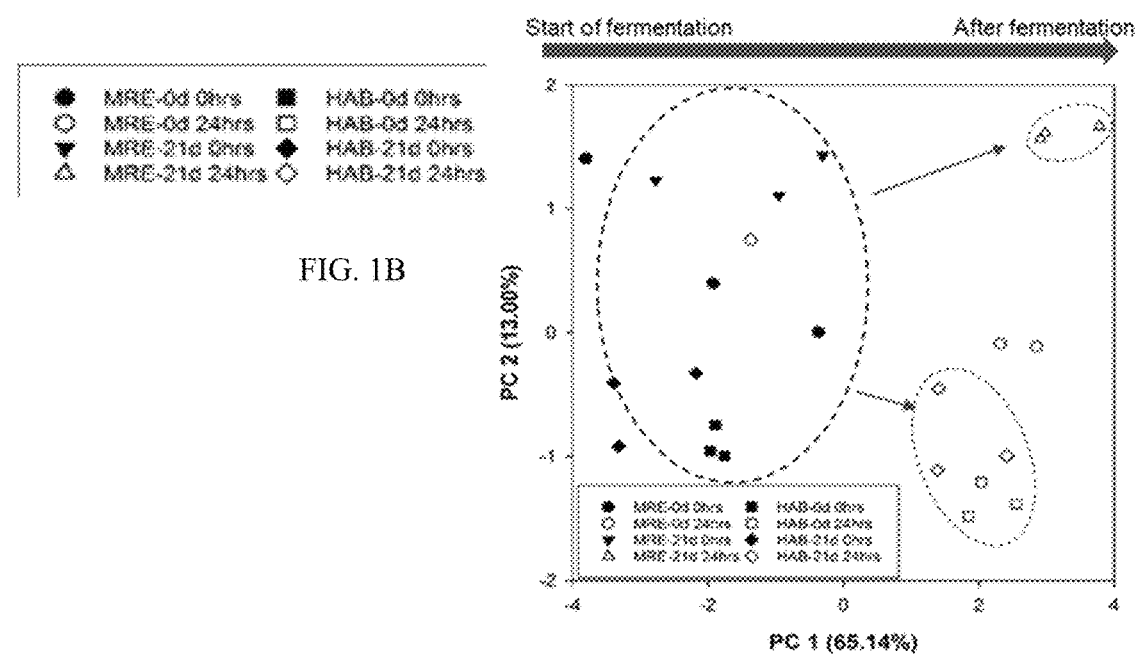
FIG. 1B is a graphic illustration of the effects of resistant starch supplementation on microbial inter-species competition and metabolism by diet-perturbed microbiota within a single colonic domain.

The fermentation model facilities correlation of generated beneficial metabolites with specific gut microbiota, which is critical information when determining intervention strategies to benefit health and performance. FIG. 1B shows the value of in vitro fermentation in exploring not just the microbial community members, but how the functional metabolism of those select microbes is varying as a function of diet-induced changes to the gut microbiota. The large intestine model was seeded with samples from volunteers under a habitual diet and exposed to a sudden change in diet with sole sustenance on a military ration. Analysis of a subset of microbes indicate that the diet change did not alter the microbial abundance and composition; however, interspecies competition for resistant starch varied as a function of the diet. Without the large intestine fermentation model, the diet-induced changes to functional microbial metabolism would not have been realized. This illustrates the synergistic nature of in vitro and human studies that can be beneficial when understanding the dynamics within the gut microbiome and developing microbiome solutions. In this particular case, resistant starch was also identified as a candidate for building resiliency to stress-induced changes to gut microbiota.

Simplified or mock communities are currently employed to deconstruct the complexities of the gut microbiome and understand microbial interactions. Articles incorporate simplified communities, but typically communities based on the most abundant taxa and limited to use of mock communities as standards for methods development (e.g., sequencing validation) or co-culture for production of chemical compounds. A microbial mixture using fermentation to identify functional relationships and assembly of a microbial ensemble to characterize at least one target biological property (e.g. resistance to colonization by enteric pathogens) in a target biological environment is illustrated in prior art; however, this work does not establish a simplified community. The rationally-designed communities to study specific functional relationships with a simplified community is one aspect of the present disclosure that is not known or used in prior GI models.

Figure 2A:
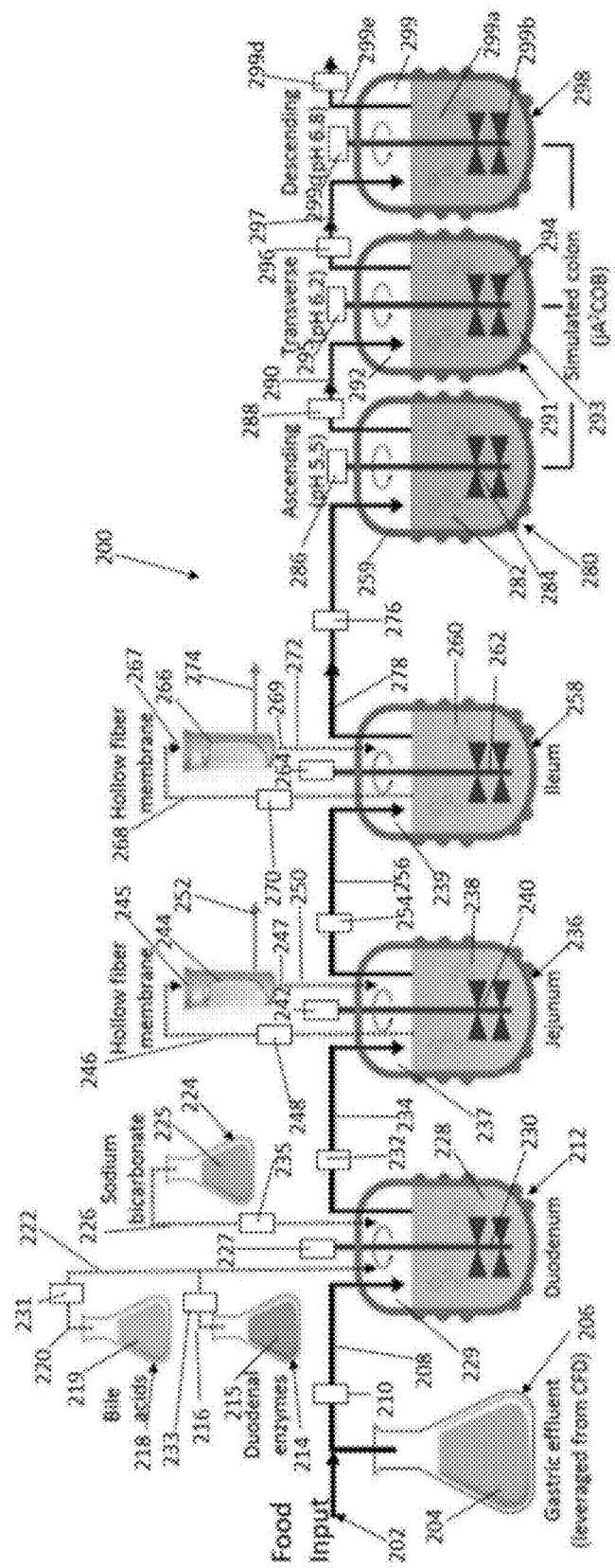
FIG. 2A is a schematic illustration of one embodiment of an in vitro model of an in vivo gastrointestinal tract of the present disclosure.

Aspects of the present disclosure include embodiment model in which a small intestine model is connected to a large intestine model, which is already completed and implemented experimentally. When integrated, one embodiment of the small and large intestine models forming a lower GI tract model with continuous flow between domains of both small and large intestines is shown in FIGS. 2A-2C. One aspect of the resulting integrated model enables the investigation of new nutrient components independently and as incorporated in exploratory food rations with research outcomes in terms of their impact on the small and large microbiome composition, metabolism, and their various metabolites after biotransformation during passage through the model.

Embodiments of the present disclosure, including that illustrated in FIG. 2A model specific conditions representing the duodenum, jejunum, and ileum in separate vessels connected by peristaltic pumps. The volumes, pH range, and transit time of each vessel are included herein or known. At discrete intervals, effluent from the gastric model can be dispensed into the duodenum chamber. The DASgip trigger system can be utilized to automate addition of pancreatic juice and bile to the duodenum (triggered by pH decrease) as well as semi-continuous transit between vessels (triggered by increase in vessel volume). Additional pumps connected to the jejunum and ileum vessels can lead to hollow-fiber ultrafiltration membranes for tangential-flow filtration. To regulate bile concentration in the distal model small bowel, chyme in the jejunum can be diluted using a solution containing 1.55% bile, whereas the ileum diluent will contain no bile.

Digestion and bioaccessability of dietary inputs is partially determined by the other components of the food matrix; however, simplified food components, (e.g., maltodextrin, whey protein, or casein) can serve as representative carbohydrates, proteins, lipids, and other nutritional components during model development, including known amounts of each component contained therein for analysis of samples from the GI model of FIG. 2 subsequently. Synthetic digestive fluids representing oral, gastric, and duodenal juices can also be use in the gastric model embodiments of the present disclosure. For example, each synthetic digestive fluid can contain a mixture of organic and inorganic compounds supplemented with enzymes and coenzymes pertinent to the specific stage of digestion (amylase in the oral fluid, pepsin in the gastric fluid, etc.). In a modified procedure, food matrices can be exposed to and incubated with each digestive fluid in turn. The embodiments of the present disclosure can leverage the oral and gastric digestive fluids developed for other gastric models as a pretreatment for food components prior to their use in the small bowel model. The input can be dispensed into the duodenum vessel at discrete intervals for a multi-stage system. The small bowel effluent and microbiome can be sampled and characterized before and after digestion of each dietary input. Analytical techniques routinely employed can be the primary methods to gauge system development. Microbial population dynamics through 16s rRNA sequencing and denaturing gradient gel electrophoresis (DGGE) can be used for the investigation. Both the jejunum and ileum growth dynamics can be monitored; low bacterial population and rapid turnover preclude growth measurement in the duodenum. To assess stability of the small bowel model microbiome in the continuous multi-stage system, the model can be operated for several days, during which DGGE and 16s rRNA samples will be collected daily. If more time-sensitive analysis of population stabilization is required, selective plating techniques can be employed to investigate population dynamics of specific, predominant microbial groups (e.g. coliforms, Clostridia, and Lactobacilli). Another alternative would be to employ PCR analysis. Effluent supernatants and dialysates from the jejunum and ileum can be collected for proximate analysis as described earlier. To assess production of SCFAs by bacterial fermentation, supernatants from the jejunum and ileum can be analyzed via gas chromatography/flame ionization detector (GC/FID). The validation of the small bowel model can be based on comparison of the breakdown products of the representative dietary components, and comparison to other lower GI model digestive behavior, in relation to derived nutrients and simple sugars.

The small bowel and colonic models can be run concurrently but separately, with effluent from the small bowel model collected and stored before incorporation into the nutrient delivery system of the colonic model. Changes to the colonic model microbiota due to introduction of ileum effluent can be characterized by 16s rRNA sequencing and/or DGGE. Analytical techniques used to evaluate the different samples of the embodiments of the present disclosure can be used to characterize changes to the microbiome during in vitro colonic fermentation. The pumps utilized for transfer between small bowel vessels can be operated semi-continuously as described earlier, whereas the pumps utilized by the colonic model can operate continuously. The combined model can operate continuously for multiple weeks with pre-treated dietary inputs added to the duodenum at regular intervals. The colonic microbial population can be monitored using, for example, DGGE to determine stability during this period.

The embodiment of FIG. 2A includes a small and large intestine model 200 with a food product port 202 into which a food product (e.g., single-component dietary compounds (e.g., maltodextrin, whey protein), food matrix, simplified food components, dietary input or food material) can be introduced along with gastric effluent 204 from a reservoir 206, the gastric effluent having a pH of about 2. Gastric effluent may include, for example, the following in g/L: NaCl 0.08, $KH_2PO_4$ 0.04, $K_2PO_4$ 0.04, $MgSO_4*7H_2O$ 0.008, $CaCL_2*2H_2O$ 0.008 and $NaHCO_3$ 0.4 in water. The first three fermentation vessels model the duodenum, the jejunum and ileum of the small intestine and are under aerobic conditions with a headspace gas of, for example, about 10% carbon dioxide, from about 1.5% to about 4% oxygen and the rest of the gas being nitrogen. The combined food product and gastric effluent can be transported using conduit 208 and pump 210 into a first vessel 212 that models the duodenum of the small intestine at a flow rate, for example, in the range of from about 5 mL/min to about 50 mL/min. Reservoir 214 including duodenal enzymes 215 is connected by fluid line 216 and reservoir 218 including bile acids 219 is connect by fluid line 220 and both fluid line 216 and fluid line 220 are connected to fluid line 222, the latter connect to the first vessel in order to supply the duodenal enzymes to the first vessel. Bile acids may include, for example, 24 g/L bile salts or oxgall bile in water. Duodenal enzymes may include, for example, the following in g/L: lipase 1.5 and pancreatin 3.6 in water. Reservoir 224 including sodium bicarbonate 225 is connected to the first vessel via fluid line 226. Sodium bicarbonate may include, for example, $NaHCO_3$ 50 g/L in water. Other embodiments can include each of reservoirs 214, 218 and 224 in other connection configurations including separately added through 3 different fluid lines, all connected to a single fluid line. Another embodiment could include the sodium bicarbonate and bile acids combined into a single reservoir.

The contents 228 of the first vessel 212 before the combined food product and gastric effluent are added can include an aqueous phosphate buffered solution. Headspace gas 229 is also present. Once the combined food product and gastric effluent are added to the contents 228 of the first vessel 212, the bile acids 219 from reservoir 218 using pump 231 and duodenal enzymes 215 from reservoir 214 using pump 233 are added to the contents 228 of the first vessel 212 and sodium bicarbonate 225 from reservoir 224 using pump 235 can be added to adjust the pH therein. The contents 228 then remain the first vessel 212 for a period of time ranging from about 15 minutes to about 120 minutes. The contents 228 of the first vessel 212 can be mixed using agitator 230 that is moved by motor 227, for example, in a rotational motion, at speeds ranging from about 50 rpm to about 150 rpm to, for example, simulate peristaltic activity within the GIT. Contents 228 can be maintained using the sodium bicarbonate at a pH, for example, ranging from about 5.0 to about 7.5. In one embodiment, the process steps for the duodenum include adding in order gastric effluent with "meal" (i.e., food product) to first vessel 212, adding sodium bicarbonate to first vessel 212 until pH=6.5 (~1/10th of gastric effluent volume), adding bile acids and duodenal enzyme solutions to first vessel 212 (~1/10th of gastric effluent volume) and pumping the contents 228 of first vessel 212 to second vessel 236 jejunum such that mean duodenum retention time is about 30 minutes. Samples of contents 228 can be removed at any time during the process from first vessel 212 for testing via a sampling port.

After the period of time mentioned above, pump 232 and fluid line 234 transport contents 228 from first vessel 212 to a second vessel 236 that models the jejunum of the small intestine at a flow rate, for example, in the range of from about 2 mL/min to about 20 mL/min. Headspace gas 237 is also present. The contents 238 of the second vessel 236 before the contents 228 of the first vessel 212 are added can include an aqueous phosphate buffered solution, a small amount of bile acids (resulting in a concentration of between about 0.2 weight % and about 2 weight %), a small amount of growth medium (e.g., brain heart infusion medium or peptone yeast glucose medium) resulting in a concentration of between about 10% and about 50%, and a complex or simplified mock community of aerobic and aerotolerant microorganisms at a concentration ranging from about $10^5$ CFU/mL to about $10^6$ CFU/mL. The order in which these components are added is diluent, growth medium, complex or simplified mock community, and contents 228 from first vessel 212. The reason for the dilution of growth medium is to allow for a small growth rate (e.g., less than $10^7$ CFU/mL) so as not to substantially increase the population of the microorganisms in the vessel. Once the contents 228 from the first vessel 212 are added to the contents 238 of the second vessel 236, the contents 238 then remain the second vessel 236 for a period of time ranging from about 1.5 hours to about 3 hours. The contents 238 can be mixed using agitator 240 that is moved by motor 242, for example, in a rotational motion, at speeds ranging from about 50 rpm to about 200 rpm to, for example, simulate peristaltic activity within the GIT. From about 10 minutes to about 150 minutes after contents 228 have been added to contents 238, jejunum diluent is added at a flow rate, for example, in the range of from about 1 mL/min to about 5 mL/min, and membrane unit 244 (e.g., a hollow fiber membrane unit, a tangential flow filtration system) which is connected to the second vessel 236 using fluid line 246 with pump 248 connected to membrane unit inlet 245 and supplies contents 238 to membrane unit 244 at a flow rate, for example, in the range of from about 50 mL/min to about 500 mL/min. The jejunum diluent may include, for example, the following in g/L: $NaH_2PO_4$ 6.6, $Na_2HPO_4$ 7.0 and bile salts 0.8 in water. As an alternative embodiment, membrane unit 244 and pump 248 may be integrated into a single unit. Membrane unit 244 can extract nutrients included in contents 238 that passes through membrane unit 244 and that which is not extracted is then be returned to second vessel 236 using fluid line 250 that is connected between membrane unit outlet 247 and second vessel 236. The extracted nutrients, such as for example, monosaccharides, lipids, and amino acids, then exit membrane unit 244 through membrane unit exit port 252. Samples of the nutrients extracted by membrane unit 244 can be obtained from membrane unit exit port 252 and tested. Samples of the contents 238 can additionally be removed at any time during the process from second vessel 236 for testing via a sampling port. The pH of contents 238 can be maintained at a pH, for example, in the range of from about 5.0 to about 8.0. In one embodiment, the process steps for the jejunum include adding in order add jejunum diluent at rate of 1-2 mL/min for 2.5 hours to second vessel 236, in parallel therewith, pump jejunum contents 238 through hollow fiber membrane and pump contents 228 in first vessel 212 to third vessel 258 such that mean jejunum retention time is about 2.5 hours.

After the period of time mentioned above, pump 254 and fluid line 256 transport contents 238 from second vessel 236 to a third vessel 258 that models the ileum of the small intestine at a flow rate, for example, in the range of from about 2 mL/min to about 20 mL/min. Headspace gas 239 is also present. The contents 260 of the third vessel 258 before the contents 238 of the second vessel 236 are added can include an aqueous phosphate buffered solution, a small amount of growth medium resulting in a concentration of between about 10% and about 50%, and a complex or simplified mock community of aerobic and anaerobic microorganisms at a concentration ranging from about $10^6$ CFU/mL to about $10^7$ CFU/mL. The order in which these components are added is diluent, growth medium, complex or simplified mock community, and contents 238 from first vessel 236. The ileum mock community media is in a common growth medium such as brain heart infusion (BHI) or peptone yeast glucose (PYG). Once the contents 238 from the second vessel 236 are added to the contents 260 of the third vessel 258, the contents 260 then remain the third vessel 258 for a period of time ranging from about 2 hours to about 5 hours. The contents 260 can be mixed using agitator 262 that is moved by motor 264, for example, in a rotational motion, at speeds ranging from about 50 rpm to about 200 rpm to, for example, simulate peristaltic activity within the GIT. From about 10 minutes to about 240 minutes after contents 238 have been added to contents 260, ileum diluent is added at a flow rate, for example, in the range of from about 1 mL/min to about 5 mL/min, and membrane unit 266 (e.g., a hollow fiber membrane unit, a tangential flow filtration system) which is connected to the third vessel 258 using fluid line 268 with pump 270 connected to membrane unit inlet 267 and supplies contents 260 to membrane unit 266 intestine at a flow rate, for example, in the range of from about 50 mL/min to about 500 mL/min. The ileum diluent may include, for example, the following in g/L: $NaH_2PO_4$ 4.4 (creates 0.1M phosphate buffer at pH 7.2) and $Na_2HPO_4$ 9.4 in water. As an alternative embodiment, membrane unit 266 and pump 270 may be integrated into a single unit. Membrane unit 266 can extract nutrients included in contents 260 that passes through membrane unit 266 and that which is not extracted is then be returned to third vessel 258 using fluid line 272 that is connected between membrane unit outlet 269 and second vessel 236. The extracted nutrients, such as for example, monosaccharides, lipids, and amino acids, then exit membrane unit 266 through membrane unit exit port 274. Samples of the nutrients extracted by membrane unit 266 can be obtained from membrane unit exit port 274 and tested. Samples of the contents 260 can additionally be removed at any time during the process from third vessel 258 for testing via a sampling port. The pH of contents 260 can be maintained at a pH, for example, in the range of from about 6.5 to about 7.5. In one embodiment, the process steps for the ileum include adding in order contents 238 from second vessel 236 to third vessel 258, add ileum mock community to the third vessel 258 and grow to mid-log phase, after transfer of contents 260 from second vessel 258 to third vessel 258, add ileum diluent at rate of 1-2 mL/min for 4 hours, in parallel with adding ileum mock community to the third vessel 258, pump ileum contents 260 through hollow fiber membrane and pump contents 260 in third vessel 258 to fourth vessel 280 such that mean ileum retention time is about 4 hours. Membrane units 244 and 266 can be the same extracting the same nutrients from their respective vessels, however, different amounts of those nutrients will be extracted from the vessels to which each are connected.

In this embodiment, the next three fermentation vessels that are connected in series model the large intestine including ascending, transverse and descending portions thereof. The three vessels modeling the large intestine are maintained under anaerobic conditions with a headspace gas of nitrogen.

After the period of time mentioned above, pump 276 and fluid line 278 transport contents 260 from third vessel 258 to a fourth vessel 280 that models the ascending portion of the large intestine at a flow rate, for example, in the range of from about 20 mL/hr to about 100 mL/hr and the ascending portion is maintained at a pH of about 5.5. Headspace gas 259 is also present. The contents 282 of the fourth vessel 280 before the contents 260 of the third vessel 258 are added can include growth medium (e.g., complex colonic medium, CCM) at a volume ranging from about 200 mL to about 600 mL and addition to a complex or simplified mock community of anaerobic microorganisms at a concentration ranging from about $10^8$ CFU/mL to about $10^{10}$ CFU/mL including, for example, a fecal extracted slurry. Once the contents 260 from the third vessel 258 are added to the contents 282 of the fourth vessel 280, the contents 282 then remain the fourth vessel 280 for a period of time ranging from about 6 hours to about 15 hours. Samples of the contents 282 can be removed at any time during the process from fourth vessel 280 for testing via a sampling port. The contents 282 can be mixed using agitator 284 that is moved by motor 286, for example, in a rotational motion, at speeds ranging from about 50 rpm to about 20 rpm to, for example, simulate peristaltic activity within the GIT.

After the period of time mentioned above, pump 288 and fluid line 290 transport contents 282 from fourth vessel 280 to a fifth vessel 291 that models the transverse portion of the large intestine at a flow rate, for example, in the range of from about 20 mL/h to about 50 mL/h and the transverse portion is maintained at a pH of about 6.2. Headspace gas 292 is also present. The contents 293 of the fifth vessel 291 before the contents 282 of the fourth vessel 280 are added can include the same or different growth medium at the same range of volumes and addition to the growth medium of the same or different complex or simplified mock community of anerobic microorganisms at the same range of concentrations as added in the fourth vessel 280. Once the contents 282 from the fourth vessel 280 are added to the contents 293 of the fifth vessel 291, the contents 293 then remain the fifth vessel 291 for a period of time ranging from about 12 hours to about 24 hours. Samples of the contents 293 can be removed at any time during the process from fifth vessel 291 for testing via a sampling port. The contents 293 can be mixed using agitator 294 that is moved by motor 295, for example, in a rotational motion, at speeds ranging from about 50 rpm to about 200 rpm to, for example, simulate peristaltic activity within the GIT.

After the period of time mentioned above, pump 296 and fluid line 297 transport contents 293 from fifth vessel 291 to a sixth vessel 298 that models the descending portion of the large intestine at a flow rate, for example, in the range of from about 20 mL/h to about 50 mL/h and the descending portion is maintained at a pH of about 6.8. Headspace gas 299 is also present. The contents 299a of the sixth vessel 298 before the contents 293 of the fifth vessel 291 are added can include the same or different growth medium at the same range of concentrations and addition to the growth medium of the same or different complex or simplified mock community of anaerobic microorganisms at the same range of concentrations as in the fourth vessel 280 and fifth vessel 291. Once the contents 293 from the fifth vessel 291 are added to the contents 299a of the sixth vessel 298, the contents 299a then remain the sixth vessel 298 for a period of time ranging from about 12 hours to about 24 hours. Samples of the contents 299a can be removed at any time during the process from sixth vessel 298 for testing via a sampling port. The contents 299a can be mixed using agitator 299b that is moved by motor 299c, for example, in a rotational motion, at speeds ranging from about 50 rpm to about 200 rpm to, for example, simulate peristaltic activity within the GIT.

After the period of time mentioned above, pump 299d and fluid line 299e transport contents 299a from sixth vessel 298 out of the sixth vessel 298 and available for testing. At any specific given residence time, samples are acquired from fermentation vessels for downstream analysis.

FIGS. 2B and 2C includes parameters of the mode stages and timeline as well as experimental parameters for operational embodiments of the embodiment of FIG. 2A. FIG. 2D includes continuous mode parameters of the large intestine model. FIG. 2E includes the differences between dynamic batch mode parameters and continuous mode parameters of the large intestine model. In order to provide further detail, continuous mode parameters of the large intestine model are designed to do model each domain sequentially with parameters designed to maximize similarity to an in vivo large intestine for the purpose of characterization of detailed biotransformation of nutrients over an extended period of time. In contrast, dynamic batch mode parameters of the large intestine model are designed to simulate several parallel replicates of a single domain for the purpose of initial screening of nutrients and inputs prior to more prolonged characterization during continuous mode.

Another alternative embodiment is shown in FIG. 2F that includes the system exemplified in FIG. 2A, however, at least one of the three fermentation vessels that are included in the large intestine portion of the model (i.e., the fourth vessel 280 that models the ascending portion of the large intestine, the fifth vessel 291 that models the transverse portion of the large intestine and the sixth vessel 298 that models the descending portion of the large intestine) may also include membrane unit as exemplified in FIG. 2F. FIG. 2F includes a fermentation vessel 300 with contents 302. Membrane unit 304 (e.g., a hollow fiber membrane unit, a tangential flow filtration system) is connected to the vessel 300 using fluid line 306 with pump 308 connected to membrane inlet 310 and supplies contents 302 to membrane unit 304 at a flow rate, for example, in the range of from about 50 mL/min to about 500 mL/min. As an alternative embodiment, membrane unit 304 and pump 308 may be integrated into a single unit. Membrane unit 304 can extract byproducts of microbial metabolism included in contents 302 that passes through membrane unit 304 and that which is not extracted is then be returned to vessel 300 using fluid line 312 that is connected between membrane unit outlet 314 and vessel 300. The extracted byproducts of microbial metabolism include, for example, SCFAS which can be absorbed in vivo through the large intestine. The extracted byproducts then exit membrane unit 304 through membrane unit exit port 316. Samples of the byproducts extracted by membrane unit 304 can be obtained from membrane unit exit port 316 and tested.

Testing (also referred to herein as analyzing, analysis or a similar description) on the samples from membrane units 244 and 266 can include, for example, colorimetric assays to detect sugars, small proteins, and fatty acids, gas or liquid chromatography to detect fatty acids, and enzyme-linked immunosorbent assays to detect specific biomolecules. Testing on the samples from the second vessel 236 and third vessel 258 can include, for example, 16s rRNA sequencing and qPCR for organism monitoring, gas chromatography to detect short-chain fatty acids, assays to detect specific biomolecules. Testing on the samples from the fourth vessel 280, fifth vessel 291, and sixth vessel 298 can include, for example, 16s rRNA sequencing, whole genome sequencing, SCFA, metabolomics, etc.

An alternative embodiment includes the system exemplified in FIG. 2A, however, the system terminates after vessel 280 and pump 288 and fluid line 290 are used to extract samples for testing from vessel 280. In this embodiment, vessel 280 is controlled to simulate the three portions of the large intestine over time using a control system, such as, for example, the DASgip system, to adjust the pH of the vessel so that it starts at pH 5.5, then is adjusted to pH 6.2 and them is adjusted to pH 6.8 to simulate all three portions of the large intestines. The residence times for each pH are about the same as those included above when there are three different vessels in FIG. 2 one for each of the portions of the large intestines.

In addition to emulating both passive absorption and host-mediated active transport within the small bowel, the filtration system including the membrane units disclosed herein, preferably need to resist biofouling by the resident microbiota from their respective vessels. To overcome these challenges, membranes encompassing a range of molecular weight cut-offs and filter materials will be canvased with membranes similar to, for example, TNO's TIM-1 and TIM-2 filters as a starting point. Efficacy of the membranes can be compared to absorption behavior of mammalian cell cultures and proximate analysis to inform membrane selection.

The microorganism communities used in the embodiments of the present disclosure can be simple or complex. Both small and large intestine models can utilize either a complex resident microbiome derived from human subjects, and/or a simplified mock microbial community, comprised of several cultivable organisms with known characteristics, and tailored for specific functional studies. The simplified mock community can be rationally designed to represent a sub-set of microbes to explore targeted functional aspects within gut microbiome including, but not limited to, nutrient metabolism, fate of engineered microbes, specific biomarker discovery, and upregulation of novel pathways. The rational assembly method of simplified mock communities, an example of which is shown below, enables elucidation of specific functions and microbe-microbe interactions, and can be tailored based on specific study goals.

An approach for the rational design of a simplified mock community for exploring engineered probiotics is to integrate selected microorganisms into a community that can be studied using the embodiment of the present disclosure. For example, a single microorganism can be combined with a different microorganism integrated into a pairwise community of the two microorganisms. A next step can be to integrate the two bacteria into a community of multiple microorganisms the community that includes, for example, 5-10 different microorganisms that can be studied with the embodiments of the present disclosure. The next step can be used to study a complex gut community that can be obtained from, for example, fecal matter from one donor or multiple donors (e.g., greater than 3) that are pooled and include a large number of microorganism types that reside in the gut. Such groupings of bacteria can be used with intended use as a microbiome modulation sense and respond tool. For instance, engineered organisms are designed and assembled as a monoculture in a pristine environment but has application within a complex, competitive microbial community. A simplified community based on nutrient metabolism consisting of organisms with increasing metabolic competition for nutrients can be designed to test engineered organism function and persistence as it is translated from monoculture to communities of increasing stringency. Table 3 below, for example, outlines specific bacteria for evaluating the fate of engineered *Escherichia coli* Nissle 1917 designed to sense a quorum sensing molecule and produce GFP in response.

TABLE 3

Simplified community designed to evaluate function and persistence of an engineered probiotic by systematically increasing metabolic competition for nutrients during fermentation.
Baseline mock community candidate organisms for evaluating engineered *E. coli*

| Organism | Substrate utilization | Community dynamics |
|---|---|---|
| *Ruminoccocus bromii* | Resistant starch | Synergistic partner |
| *Roseburia intestinalis* | Large polysaccharides (limited), simple carbs | Synergistic partner |
| *Bacteroides thetaiotaomicron* | Simple starch, complex/simple carbs | Synergistic/competitor |
| *Eubacterium rectale* | Simple starch, monos, XOS | Synergistic/competitor |
| *Faecalibacterium prausnitzi* | Simple carbs, monos, oligos | Competitor |
| *Bifidobacterium animalis* | Simple carbs, monos, oligos | Competitor |
| *Lactobacillus* spp | FOS, GOS, MOS | Competitor |
| *Escherichia coli* spp. | Mono, oligos | Direct competitor |

Figure 3A:
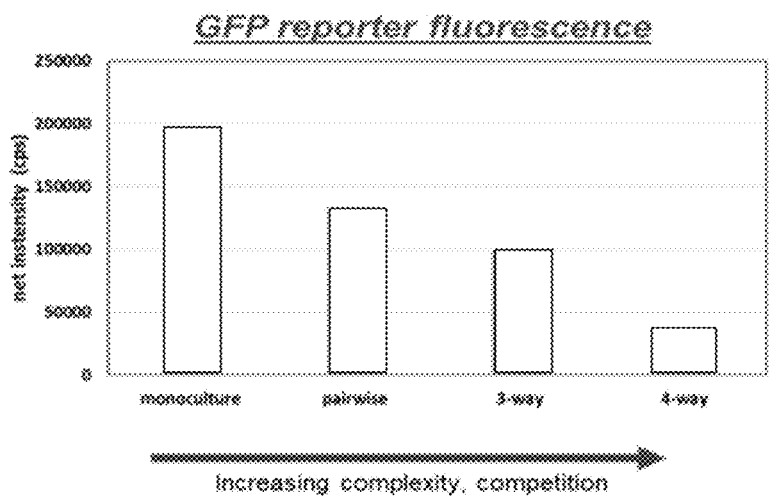
FIGS. 3A, 3B and 3C are graphic illustrations of the results of data evaluating engineered bacteria constitutive expression of Green Fluorescent Protein, (GFP), growth persistence and plasmid stability.
Figure 3B:
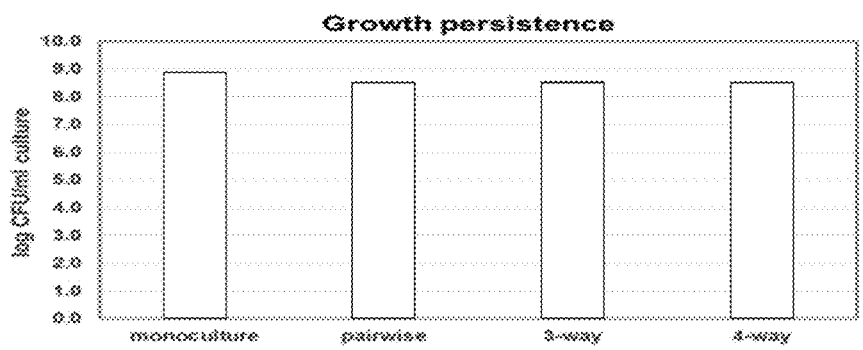
Figure 3C:
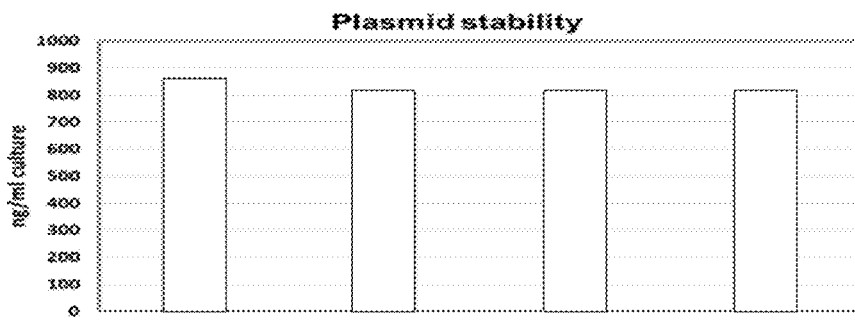

FIGS. 3A, 3B and 3C illustrate results of implementing the testing regime identified in FIG. 2D. Engineered bacteria, *Escherichia coli* Nissle 1917, constitutive expression of green fluorescent protein (GFP) is evaluated through fluorimetry and growth persistence and plasmid stability through quantitative polymerase chain reaction (qPCR). For the results included in FIGS. 3A, 3B and 3C, Fermentation vessels were seeded with bacteria grown separately and combined in equal proportions. Samples were collected at 0 and 24 h to determine GFP fluorescent function, organism growth persistence and GFP plasmid stability. For GFP fluorescence measurement, bacterial cells were pelleted by centrifugation at 16,000×g, 5 min, washed 2× with 0.9% NaCl. Pellets were lysed with Lysozyme/Tris/EDTA/Triton x-100 (LTX) solution for 30 min at 37° C. and the lysate collected by centrifugation. Fluorescence was measure at $E_x$=480 nm, $E_m$=485-600 nm on a HJY Fluorolog 3 (Horiba Scientific, Piscataway, NJ). For organism persistence and plasmid stability, bacterial DNA samples were extracted from 24 hour fermentation aliquots using the QIAMP Power Fecal DNA Extraction Kit (QIAGEN, Inc., Germantown, MD) modified by adding initial LTX treatment and quantified (ng/uL) using Nanodrop (ThermoFisher Scientific, Inc., Waltham, MA). qPCR was used to determine absolute abundance of engineered *E. coli* Nissle GFP (CFU/mL) and presence of GFP plasmid (ng/uL) using standard curves constructed using pure culture DNA. Specific sets of primers were used: 1) Mut7/8 for organism persistence (Blum-Oehler et al. (2003) *Research in Microbiology* 154 (2003) 59-66), and 2) GFPa1-f (GCAAGCTGTC-TACCGAGTTTA) and GFPa1-r (AAGGGCTTGTCGAA-GATGTAG) for plasmid stability. qPCR reactions were carried out using the 2× Forget-Me-Not qPCR Master Mix (Biotium, Hayward, CA) and the iCycler iQ Optical module (BioRad Laboratories, Hercules, CA). iCycler settings for Mut7/8 were 95° C., 2 min, and 45 cycles of 95° C. for 1 min, 60° C. for 10 sec, 72° C. for 25 sec; and for GFP plasmid were 95° C., 10 min, and 45 cycles of 95° C. for 15 sec, 51° C. for 1 min, 72° C. for 25 sec.

FIG. 3A shows linear decrease of GFP response as competition increases. Growth (FIG. 3B) and plasmid stability (FIG. 3C) are not influenced by competition, relative to monocultures.

In vivo small bowel microbiome sampling may require invasive procedures and would be difficult to obtain consistently. For the purposes of developing the model, a mock microbiome can be used including oral and fecal microbiota. In order to implement this strategy, rational design of a simplified mock community can be employed as described earlier to select commercially-available strains, with known characteristics and encompassing the major functional and taxonomic groups of the small intestine in vivo microbial population, and generate a stable polymicrobial community consisting of between 4 and 15 distinct species in which all organisms are metabolically active.

To further enhance the physiological relevance of the model, another embodiment incorporates mammalian intestinal tissue (namely, large intestine organoids) into the large intestine chambers. The supported organoids can be designed to explore real-time interface between the epithelial layer (e.g. mucin) and bacteria to garner knowledge on mucosal-associated bacteria that are pivotal to host health but not easily sampled in human studies. The organoid:microbiota interface can be generated in multiple approaches including, but not limited to, an organoid "coupon" with the organoid monolayer exposed to a separate chamber with oxygen present in order to maintain organoid viability and mucin production, while the mucin layer itself is exposed for direct interaction with gut bacteria within an anaerobic atmosphere. The "coupons" can be removed during fermentation through the head plate (e.g., FIGS. 4A, 4B, 4C and 4D) or isolated via a separate system (e.g., FIG. 5) that will be incorporated as part of the flow process (similar to small molecule removal).

Host:bacteria interface incorporates organoids or other host cells. Organoid monolayers containing intestinal stem cells can be differentiated into multiple epithelial cell types including absorptive, and secretory cell types including goblet cells which produce and secrete mucin. Organoid monolayers can have a functional and renewable mucin layer. In addition, organoids can undergo directed differentiation by which they are "driven" to become a majority of one cell type (e.g. goblet cells), therefore studying mucin-bacteria dynamics is highly possible. Microfluidic systems incorporate host components but not at interface of bacteria and not to overproduce mucin. A supported organoid monolayer with a metabolically produced mucin layer has not been incorporated in GI model systems. The incorporation of "live" mucin-producing host cell will significantly advance state of the art and physiological relevance of simulated GI models.

Figure 4A:
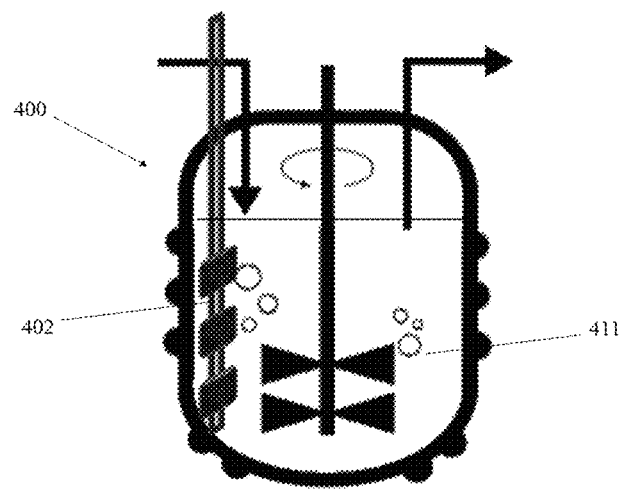
FIGS. 4A-4D are illustrations of one embodiment of a mucin producing device.
Figure 4B:
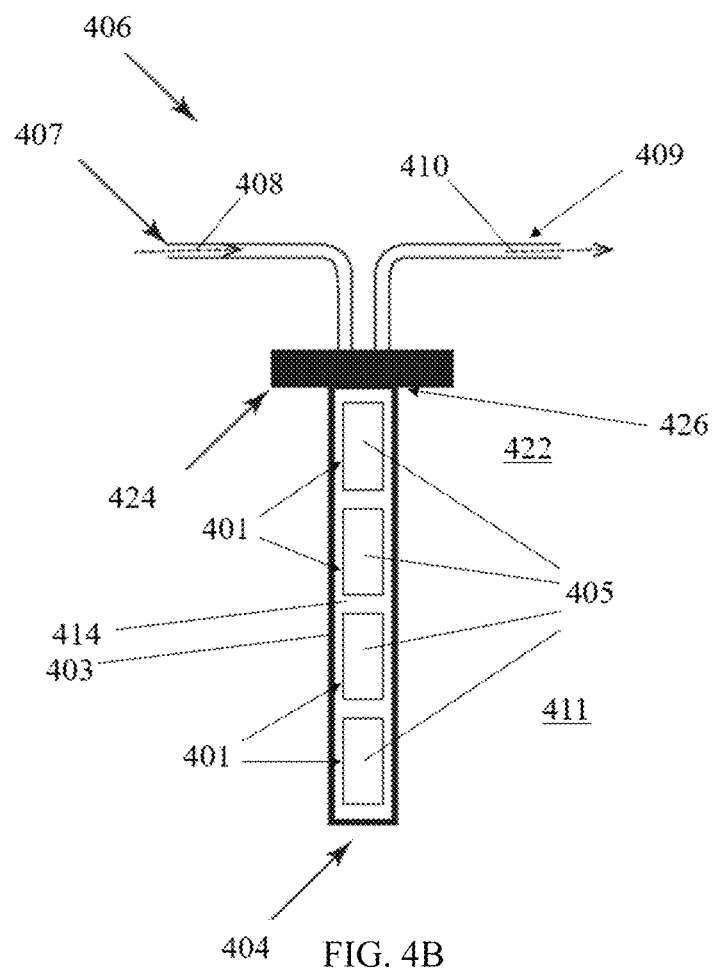
Figure 4C:
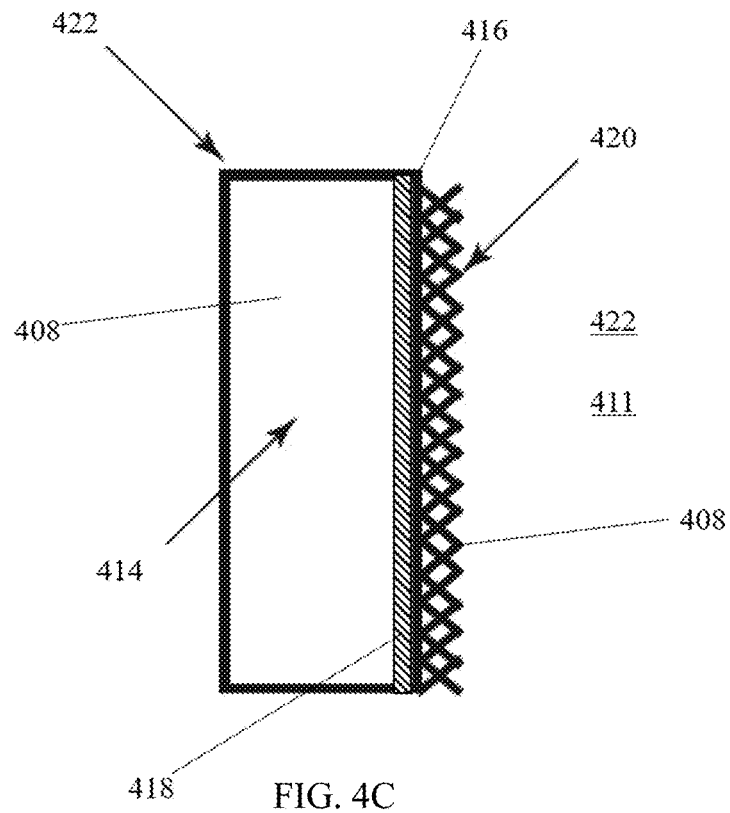
Figure 4D:
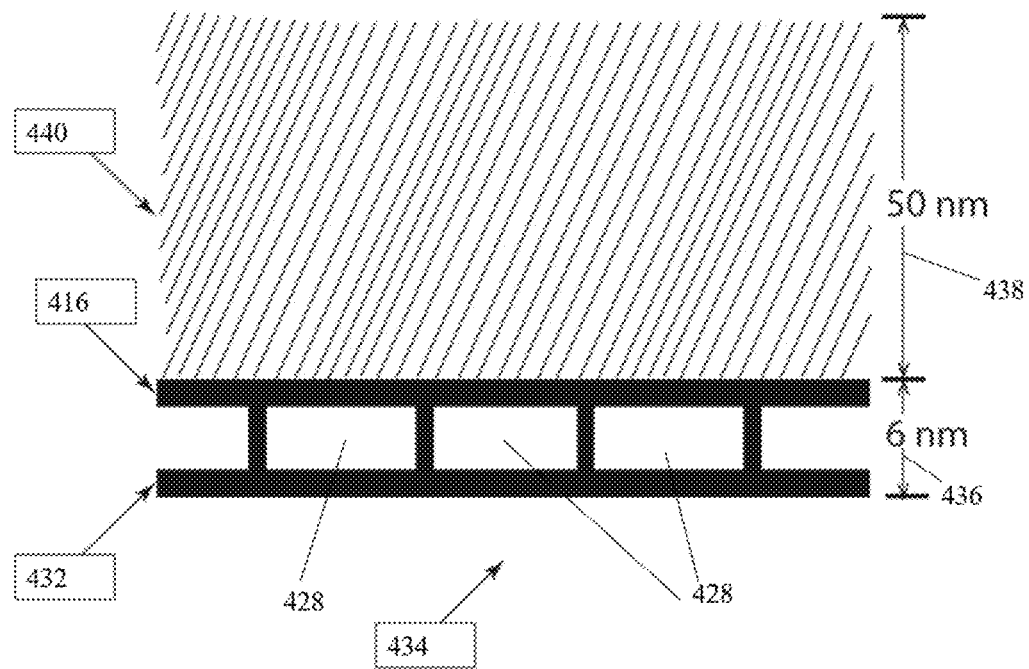

In FIGS. 4A, 4B, 4C and 4D show one embodiment of a mucin producing device that includes the supported organoids integrated in one of the large intestine vessels illustrated in FIG. 2A. FIG. 4A includes a large intestine vessel 400 similar to vessels 280, 291 and 298 in FIG. 2A. The large intestine vessel 400 includes a host cell organoid scaffold 402 that is positioned inside vessel 400 and into the contents 411, which are described in more detail above for FIG. 2A. FIG. 4B shows a more detailed illustration of one embodiment of a mucin producing device having a host cell organoid scaffold. A mucin producing device 406 includes an enclosure 404 with a fluid inlet 407 and a fluid outlet 409 for the movement of growth medium, for example, Intesticult™ or similar human cell line medium, with oxygen in the direction of arrow 408 into the enclosure 404 and arrow 410 out of the enclosure 404. The growth medium with oxygen also circulates on the interior 414 of the enclosure 404 and on one side of the host cell coupons 405. The enclosure 404 can be made of a suitable rigid material and may also be clear or opaque. Since the microorganism in the rest of the large intestine vessel are anaerobic, the growth medium with oxygen needs to be restricted to the interior 414 of the enclosure 404 as shown in FIGS. 4B and 4C. Disposed within the enclosure 404 are host cell coupons 405 that are positioned in openings 401 in the wall 403 of enclosure 404, the openings 401 of a suitable size and shape for the host cell coupons 405 to fit securely therein such that fluid does not pass between the interior 414 and exterior 422 of enclosure 404. The host cell coupons 405 may be secured in the openings 401 using, for example, snap-in holder grips. The host cell coupons 405 include an organoid monolayer of epithelial cells including mucin producing cells 418 in a matrix (for example, a Transwell® insert or similar insert) in which the host cells can grow and adhere. Prior to transferring the host cell coupons to the enclosure 404, the host cells are grown and adhere to the matrix and once the host cells have differentiated and started producing mucin, the host cells in the matrix are transferred to the enclosure 404 and inserted into vessel 400 and its contents 411. The host cells are exposed to the interior 414 of enclosure 404 on one side and a mucin-permeable membrane 416 on the opposing side of the host cells 418 to interior 414 and positioned between host cell 418 and mucin 420, mucin-permeable membrane 416, for example, a Transwell® insert or similar insert, being permeable to mucin 420 produced by the host cells 418, but not to the host cells or growth medium circulating opposite to the host cells 418 on the interior 414 of enclosure 404. The mucin 420, therefore, is positioned on the exterior 422 of enclosure 404 and exposed to the contents 411 of vessel 400 and the microorganisms included therein. The mucin producing device 406 may also include a top structure 424 through which fluid inlet 407 and fluid outlet 409 and can be connected to the top 426 of enclosure 404. FIG. 4D includes a cross-section illustration of an embodiment that is a magnified image of a single layer of host cells 428 with mucin-permeable membrane 416, matrix 432 and growth medium 434. In this particular exemplary embodiment, the thickness 436 of the host cells 428 is about 6 nm and the thickness 438 of the mucin 440 is about 50 nm. Top structure 424 could be used if mucin producing device 406 were inserted in a fermentation vessel having a headplate 800 and a headplate body 802 similar to the embodiments of the present disclosure in FIGS. 8A-8D and through one of ports therein, the top 424 being of a suitable size and shape to securely fit into one of the ports without passing entirely there through.

Figure 5:
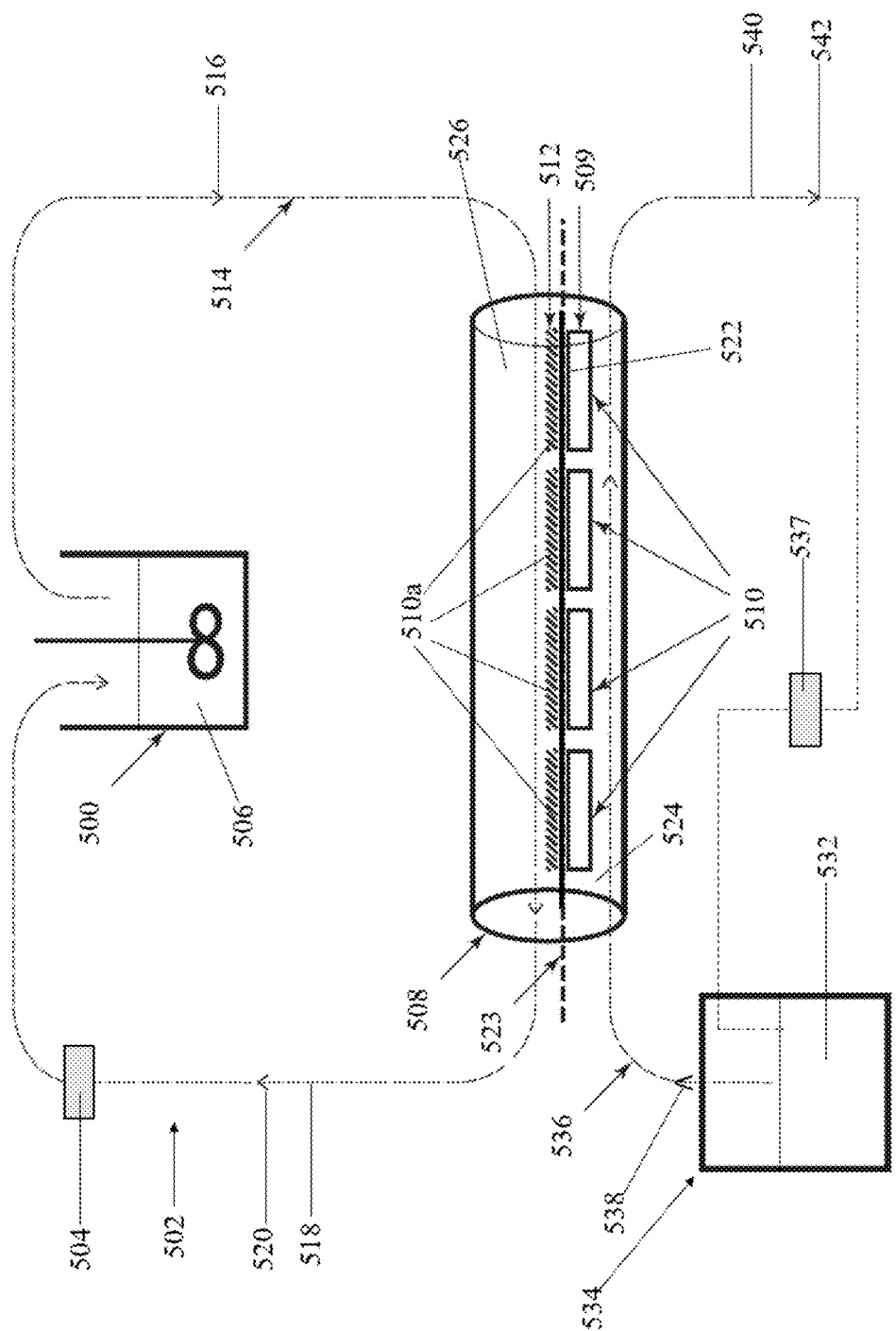
FIG. 5 is an illustration of another embodiment of a mucin producing device.

Another embodiment using host cell organoids to produce mucin is shown in FIG. 5. This embodiment includes a large intestine vessel 500 similar to vessels 280, 291 and 298 in FIG. 2A. FIG. 5 also includes an inline pump system 502 with a pump 504 to actively move liquid contents 506 containing microbiota from the vessel 500 to a separate enclosure 508 that houses the host cell organoids coupons 510. The chamber 508 is designed to allow host cell maintenance for prolonged exposure to microbiota in liquid 506 that flow to the chamber 508 in fluid line 514 in the direction of arrow 516 and actively interact with the exposed mucin layer 512 of mucin sections 510a corresponding to the positions of host cell organoids coupons 510. The mixture with the mucin then flows back to vessel 500 through fluid line 518 in the direction of arrow 520. The enclosure 508 is separated by a membrane wall 522 along an axis 523, membrane wall 522 separating enclosure 508 into interior sub-chambers 524 and 526. Sub-chamber 524 includes a monolayer 509 of the host cells (in matrix, described previously) in coupons 510 on one side of membrane 522, membrane 522 being permeable to mucin 512 produced by the host cells 510, but not to the host cells or growth medium circulating in sub-chamber 524 or liquid content 506 circulating in sub-chamber 526. The mucin 512 is positioned in sub-chamber 526 on the opposite side of membrane 522 and exposed to and travels in liquid 506 that flows back into vessel 500 via fluid line 518 and the microorganisms included therein. Growth medium 532 containing oxygen, as described previously, circulates through sub-chamber 524 from container 534 through fluid line 536 in the direction of arrow 538, enters sub-chamber 524 and returns to container 534 via fluid line 540 in the direction of arrow 542, the circulation brought about by pump 537 to actively move growth medium 532 and continuously nourish the host cells in coupons 510 so that the cells make the mucin.

Figure 6:
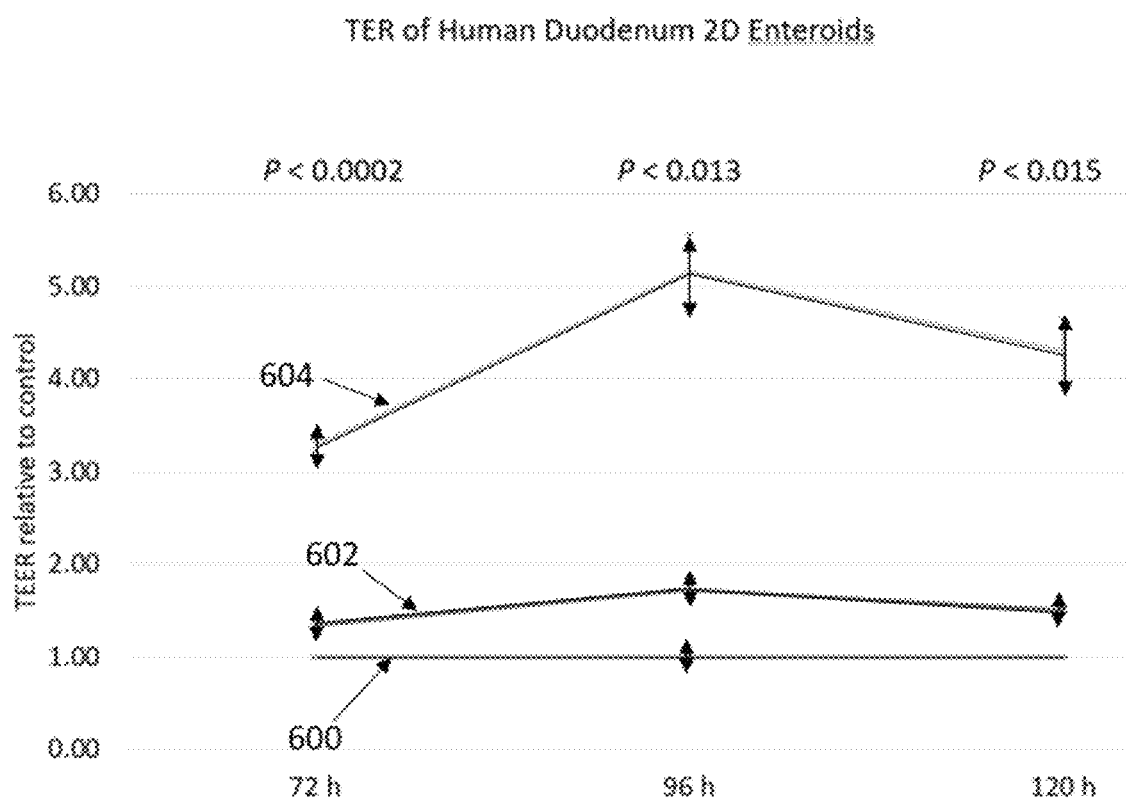
FIG. 6 is a graphic illustration of the results of fecal supernatant (FS) derived from an in vitro fermentation study under distal conditions (independent mode) exposed to 2D human duodenum organoids. Treatment with 25% FS increased barrier function, expressed as transepithelial electrical resistance (TEER) in ohms, through mucin secretion and increase in junction proteins, relative to controls (control and C59-DAPT).

In the embodiments of FIG. 4 and FIG. 5, the host cells can be sampled in real-time for exploring mucosal-associated microbes and host:microbiome response. The addition of the organoid component may significantly enhance the current state of such ex vivo systems, which currently employs mucin-containing polymer beads or within a supported 3D co-culture model that has anaerobic and complexity limitations. The organoid incorporation through these platforms not only enables exploration of mucosal-associated bacteria but also the host cell response to the generation of pro and anti-inflammatory compounds including cytokines and chemokines. Initial experimentation merging fermentation supernatants and human duodenum organoids have been initiated with permeability measurements (FIG. 6), protein and gene expression analysis. The organoids can also be manipulated to produce alternative structures of interest including other functional cell types that could be exposed to gut-derived metabolites.

After the embodiments of FIGS. 4A-4D or FIG. 5 have been utilized as part of one of the embodiments of the present disclosure, the host cells and the mucin layer may be analyzed to determine changes that may have taken place during use.

Large intestine model embodiment of the present disclosure was employed in dynamic batch mode under distal only conditions to explore biotransformation of polyphenolic compounds using a complex community derived from 3 fecal donors. As a control, polyphenol-deficient vessels were run in parallel and aliquots were removed from each vessel after 0 and 24 hrs of fermentation. The polphyenol-deficient vessel containing fecal inoculum was then centrifuged and supernatant collected and filtered to remove bacterial cells, (termed: fecal supernatants (FS)), diluted in Advanced DMEM/F12 media prior to dilution in Intesticult media, and added to 2D human duodenum organoids. The results are included in FIG. 6 in which graph 600 is the control, graph 602 is C59-DAPT and graph 604 is 25% FS. Barrier integrity was determined by using the EVOM2 (World Precision Instruments, Sarasota, FL), which measures transepithelial electrical resistance (TEER) in ohms. Measurements were taken over the course of each experiment to track growth and confluency as well as at 0 and 24 h of organoid exposure to fecal supernatant. Treatment with 25% FS increased barrier function through mucin secretion and increase in junction proteins, relative to controls (control and C59-DAPT).

Figure 7:
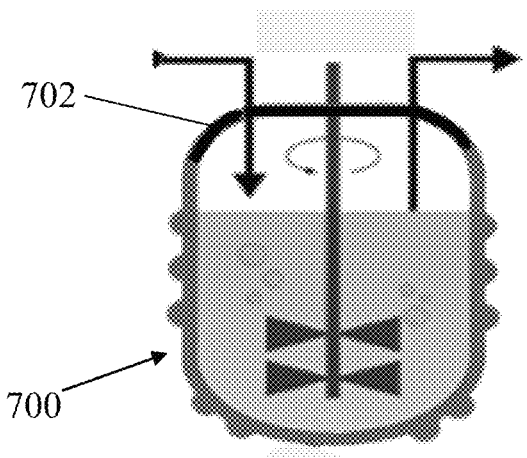
FIG. 7 is a schematic illustration of one embodiment of a fermentation vessel including a headplate.
Figure 8A:
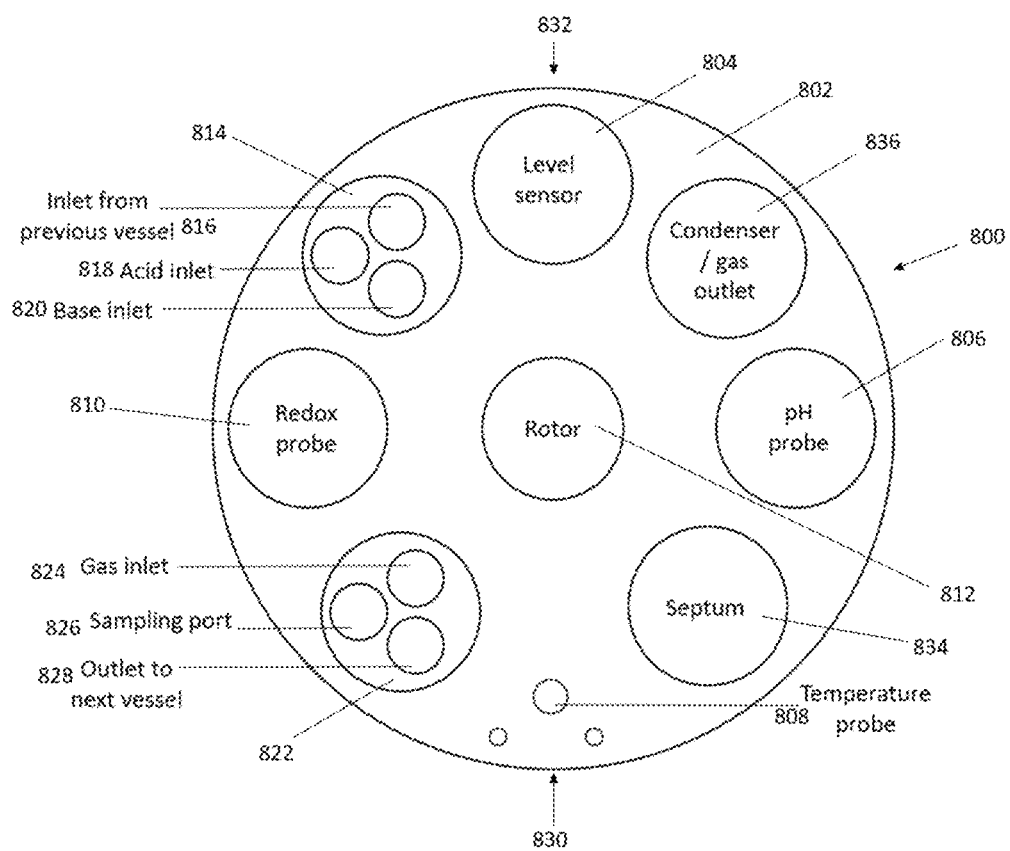
FIGS. 8A-8C are illustrations of an embodiment of a headplate.
Figure 8B:
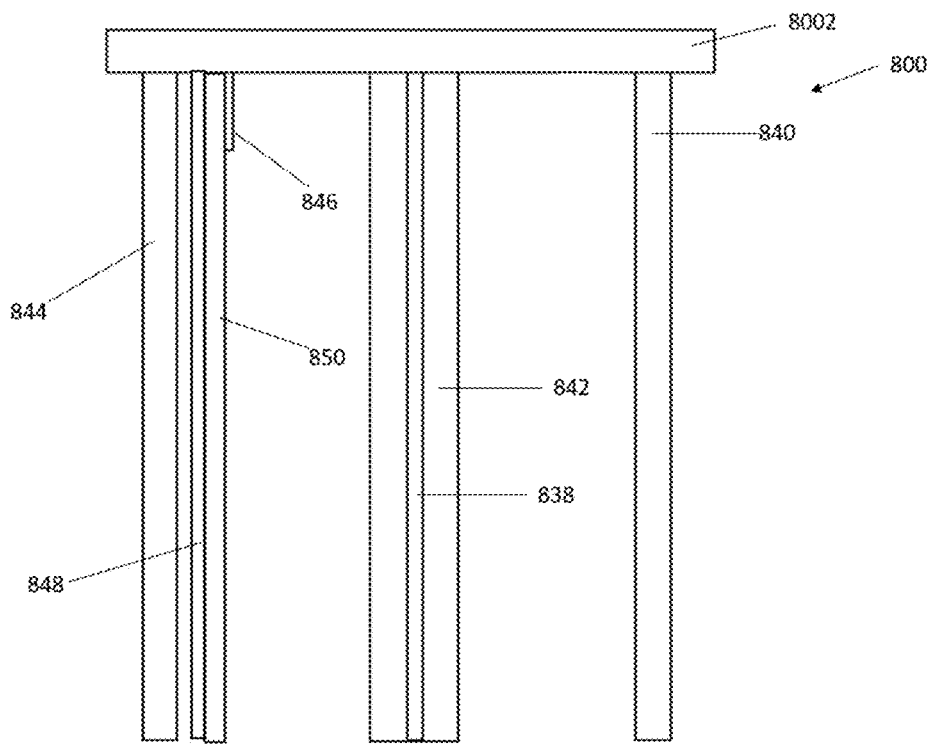
Figure 8C:
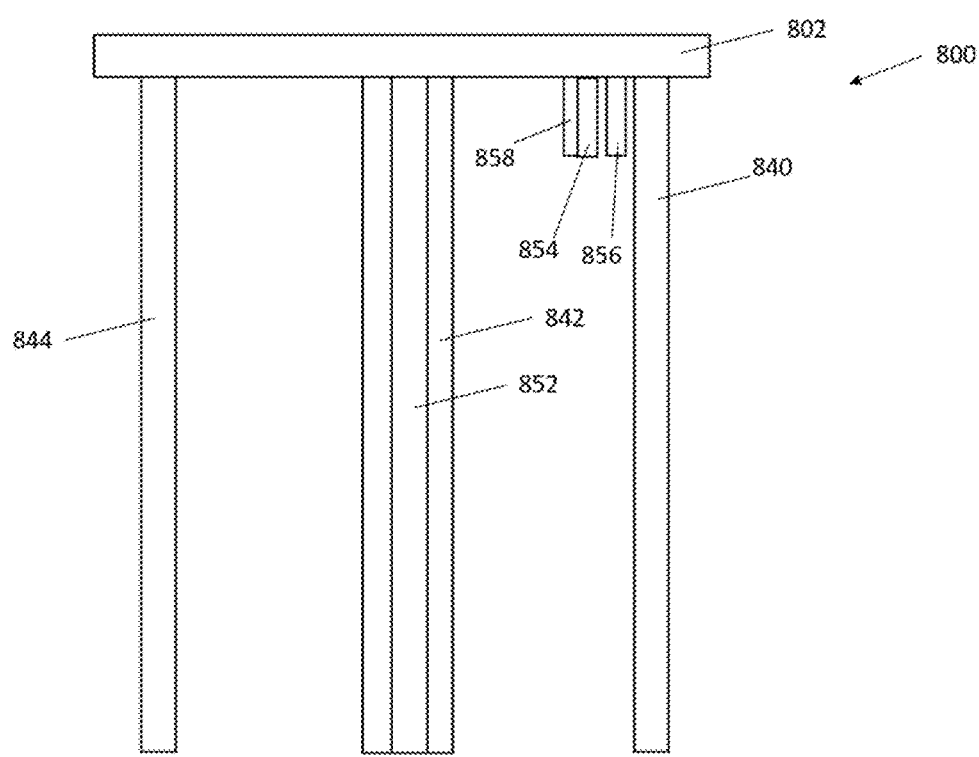

Another embodiment of the present disclosure includes a head plate that covers the top of fermentation vessels, such as, for example, first vessel 212, second vessel 236, third vessel 258, fourth vessel 280, fifth vessel 291 and sixth vessel 298 of the embodiment of FIG. 2A as well as the single vessel large intestine embodiment of FIG. 2A disclosed herein, as illustrated in FIG. 7 that includes a fermentation vessel and a headplate 702. More detail of the headplate are included in FIGS. 8A-8D. FIG. 8A includes headplate 800 a headplate body 802 with ports to components on the interior of the vessel to which the headplate is attached including a level sensor 804, a pH probe, 806, a temperature probe 808, a redox probe 810 and a rotor 812 which is connected to the agitators on the inside of the vessels and the motor on the outside of the vessels in FIG. 2A (e.g., the first vessel 212 can be mixed using agitator 230 that is moved by motor 227). Port 814 can be split into three ports including inlet from a previous vessel 816, acid inlet 818 and base inlet 820. Port 822 can be split into three ports including gas inlet 824, sampling port 826 and outlet to next vessel 828. FIG. 8B is a view of the side of headplate 800 looking in the direction of arrow 830 and FIG. 8C is a view of the side of headplate 800 looking in the direction of arrow 832. Headplate 800 also includes a septum 834 (made of, e.g., rubber or rubber-like material that provide a seal and into which the needle of a hypodermic can penetrate and upon removal re-seal and can be used to inoculate the vessel with microorganisms) and a condenser/gas outlet 836 which is open and allows head gas in the vessel to escape.

FIGS. 8B and 8C includes headplate 800 and headplate body 802 as well as the components that sit into the fermentation vessel. FIG. 8B also includes a temperature sensor dip tube 838 that includes a temperature sensor that can be connected through port 808, a pH probe 840 that can be connected through port 806, a rotor 842 that can be connected through port 812, a redox probe 844 that can be connected through port 810, a gas inlet tube 846 that can be connected to port 824, a sampling dip tube 848 that can be connected to sampling port 826, and an outlet to next vessel dip tube 850 can be connected through port 828.

FIG. 8C also includes a level sensor 852 and can be connected through port 804, rotor 842 described above, redox probe 844, pH probe 840, an inlet from previous vessel tube 854 that can be connected through port 814, an acid inlet tube 856 that can be connected through port 818, a base inlet tube 858 that can be connected through port 820.

Figure 8D:
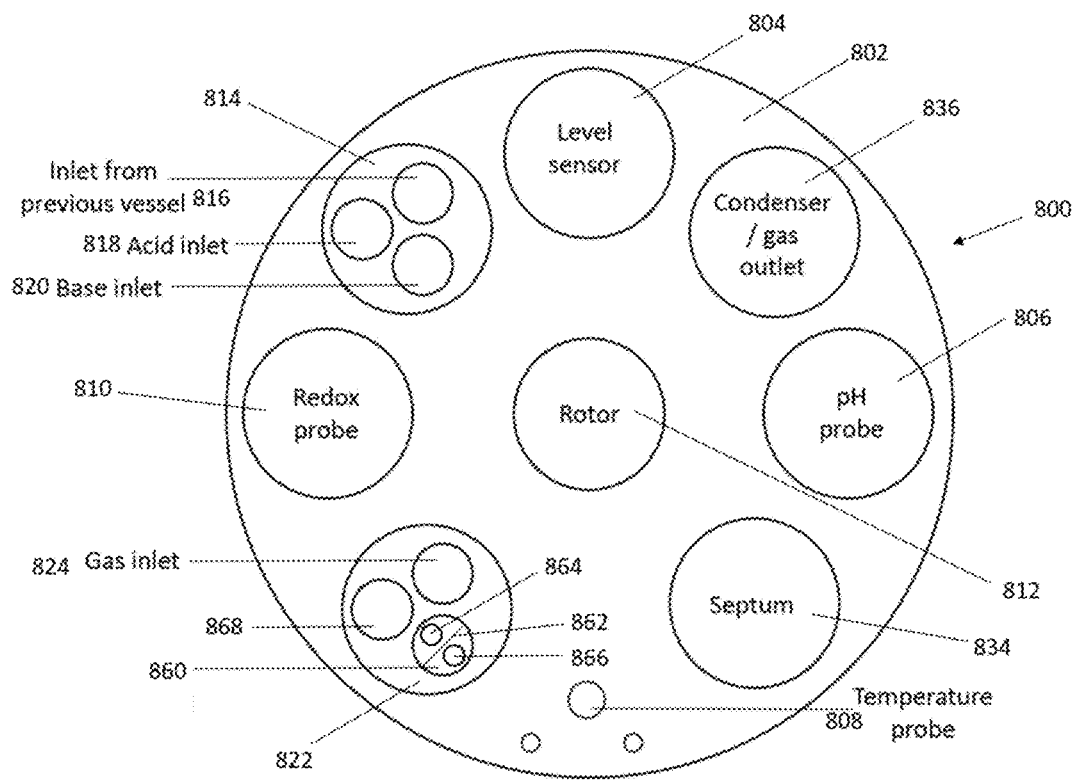
FIGS. 8D and 8E are illustrations of alternative embodiments of a headplate.

The headplate configuration illustrated in FIG. 8A can be used with fourth vessel 280, fifth vessel 291 and sixth vessel 298 of the embodiment of FIG. 2A as well as the single vessel large intestine embodiment of FIG. 2A disclosed herein. FIG. 8D illustrates another embodiment that can be used with the first vessel 212 in FIG. 2A. The FIG. 8D embodiment includes many of the same features as FIG. 8A and the same side views as FIGS. 8B and 8C. The differences include port 822 split into three ports including gas inlet 824, outlet to next vessel 828 and a third port 860. Third port 860 includes a splitter 862 to divide this port into two additional ports that include a sampling port 864 and an outlet to next vessel port 866. A duodenal enzyme port 868 is connected to a fluid line from reservoir 214 and is used to introduce duodenal enzymes 215 from reservoir 214 through the fluid line into first vessel 212. In this embodiment, acid inlet port 818 is connected to a fluid line from reservoir 218 and used to introduce bile acids 219 from reservoir 218 through the fluid line into first vessel 212 and a base inlet port 820 is connected to a fluid line from reservoir 224 and used to introduce sodium bicarbonate 225 from reservoir 224 through the fluid line into the first vessel 212.

Figure 8E:
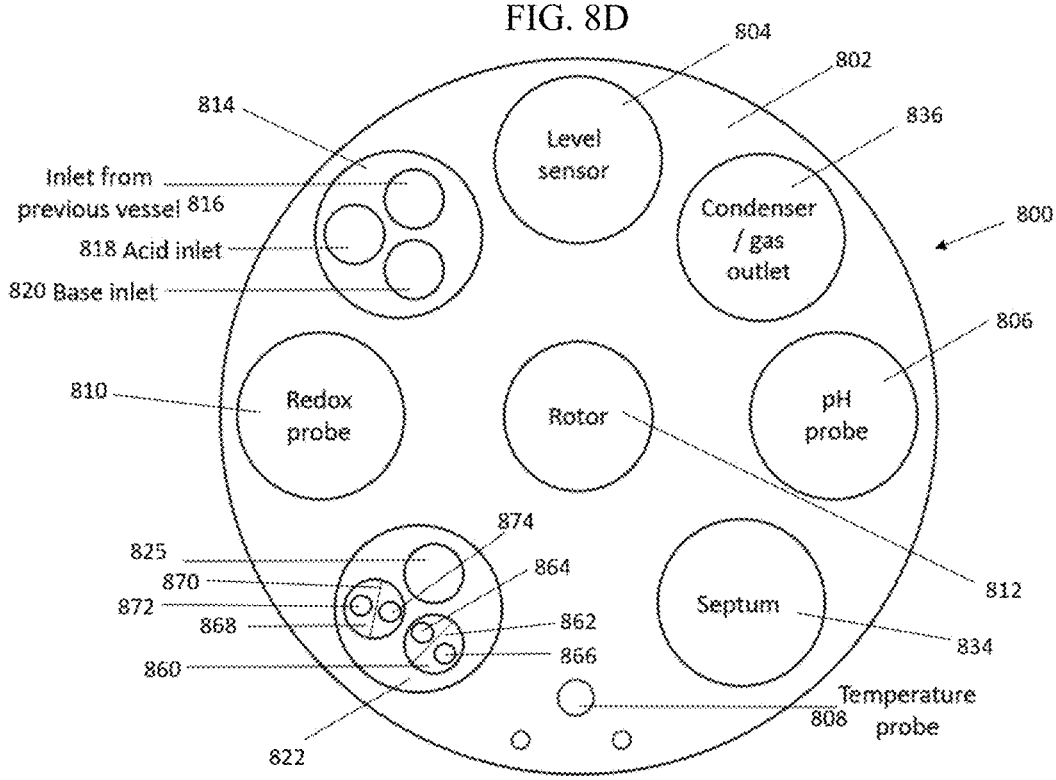

FIG. 8E illustrates another embodiment that can be used with the second vessel 226 and third vessel 258 in FIG. 2A, both of which are connected separately to a different membrane unit and where the FIG. 2F embodiment is included in the system exemplified in FIG. 2A and FIG. 2F is an embodiment of at least one of the three fermentation vessels that are included in the large intestine portion of the model (i.e., the fourth vessel 280 that models the ascending portion of the large intestine, the fifth vessel 291 that models the transverse portion of the large intestine and the sixth vessel 298 that models the descending portion of the large intestine) are connected separately to a membrane unit. The FIG. 8E embodiment includes many of the same features as FIG. 8A and the same side views as FIGS. 8B and 8C. Similar to FIG. 8D, port 822 is split into three ports including an outlet to the next vessel 825, a third port 868 and a fourth port 860. The third port 868 includes a splitter 870 to divide this port into two additional ports that include a sampling port 872 and an outlet to the membrane unit 874 as shown in FIG. 2 (e.g., fluid line 246 for second vessel 236 and fluid line 268 for third vessel 258). Port 822 is split into three ports including acid inlet 818, base inlet 820 and an inlet from the previous vessel 816. Fourth port 860 includes a splitter 862 to divide this port into two additional ports that include an inlet from the membrane unit 864 from the respective vessel as shown in FIG. 2 (e.g., fluid line 250 for second vessel 236 and fluid line 272 for third vessel 258) and a gas inlet 866. The sampling port for the embodiments of FIGS. 8A-8E can be used to provide access to the contents of a vessel, including, removal of a sample of the contents for analysis and testing thereof.

Other headplate embodiment are also included in the present disclosure where other ports which are not split (e.g., 816, 818, 820 and 824 in the embodiments of FIGS. 8D and 8E and 868 in the embodiment of FIG. 8D) can also include a splitter incorporated therewith and be split into 2 ports.

Figure 9:
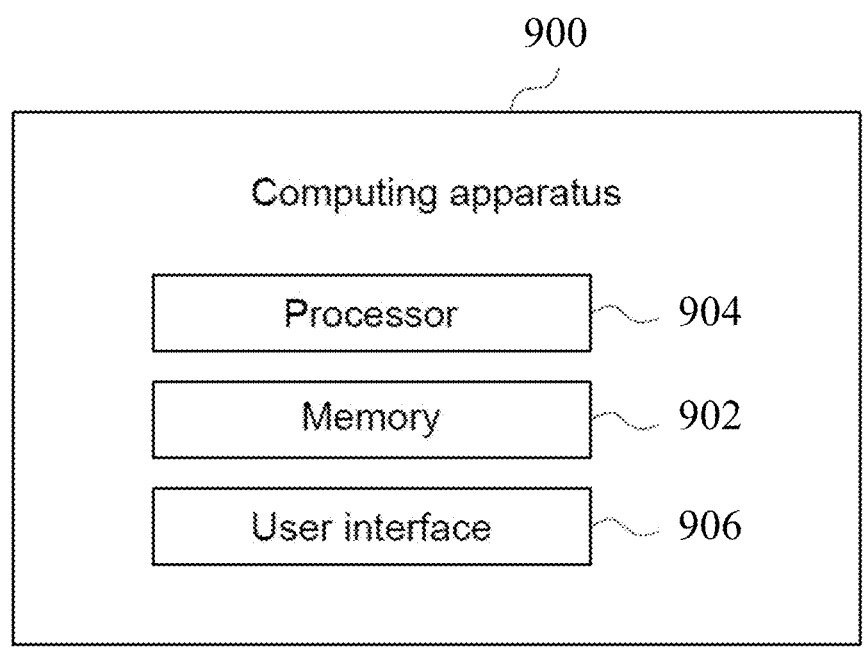
FIG. 9 illustrates a block diagram of an exemplary computing/processor apparatus included in the digital receiver/processor.

Another embodiment is a control system, for example, the DASgip system that monitors and operates certain operations of the embodiment of FIG. 2A and alternative embodiments disclosed herein, including vessel 280 controlled to simulate the three portions of the large intestine over time in a single vessel, In at least one aspect of the disclosed embodiments, the systems and methods disclosed herein may be executed by controller including one or more computers or processor-based components under the control of one or more programs stored on computer readable medium, such as a non-transitory computer readable medium. FIG. 9 shows a block diagram of an exemplary computing apparatus 900 that may be used to practice aspects of the disclosed embodiment. In at least one exemplary aspect, the digital receiver/processor and other disclosed devices, components and systems may be implemented using an instance or replica of the computing apparatus 900 or may be combined or distributed among any number of instances or replicas of computing apparatus 900.

A computing apparatus 900 may include computer readable program code or machine readable executable instructions (such as, for example, instructions to pump fluids and operate the agitator motors utilized in the embodiments disclosed herein) stored on at least one computer readable medium 902, which when executed, are configured to carry out and execute the processes and methods described herein, including all or part of the embodiments of the present disclosure. The computer readable medium 902 may be a memory of the computing apparatus 900. In alternate aspects, the computer readable program code may be stored in a memory external to, or remote from, the apparatus 900. The memory may include magnetic media, semiconductor media, optical media, or any media which may be readable and executable by a computer. Computing apparatus 900 may also include a processor 904 for executing the computer readable program code stored on the at least one computer readable medium 902. In at least one aspect, computing apparatus 900 may include one or more input or output devices to allow communication among the components of and those connected to the system model (the automated (e.g., DASgip system) parallel bioreactor platform), including, for example, operate pumps and agitator motors using what may be generally referred to as a user interface 906, such as, the operator workstation described above, which may operate the other components included in or connected to the controller of the system model (the automated (e.g., DASgip system) parallel bioreactor platform) or to provide input or output from the computing apparatus 900 to or from other components of the system model. User interface 906 may include display unit.

Figure 10A:
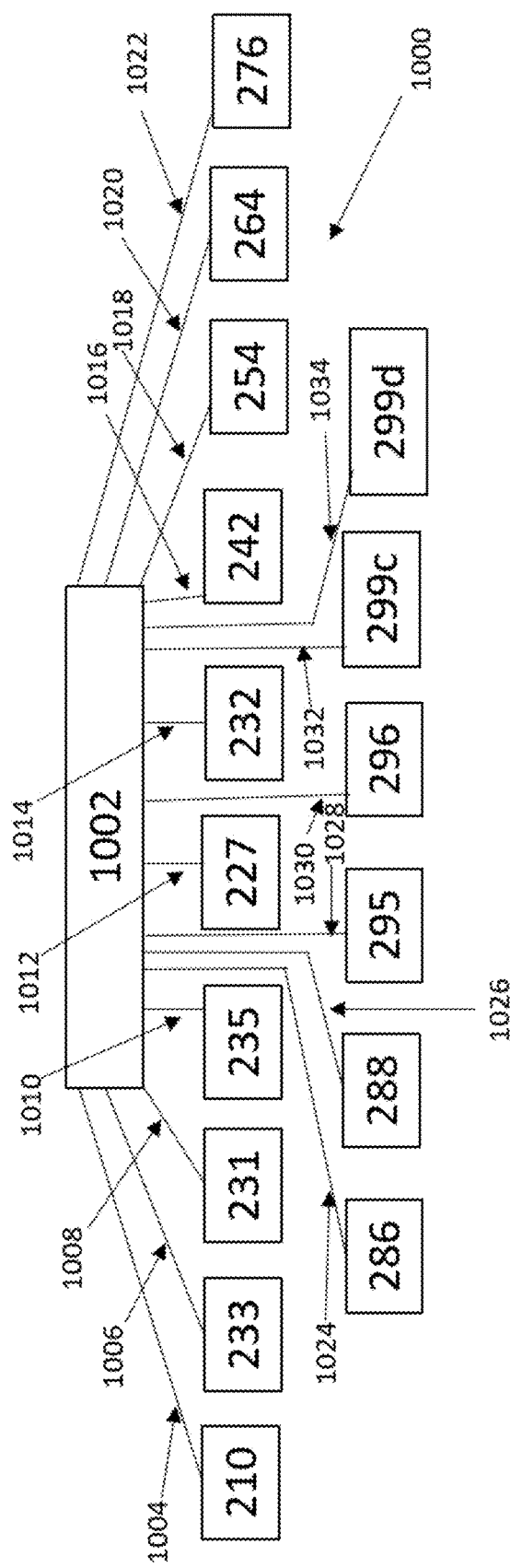
FIGS. 10A-C illustrate a block diagram of exemplary embodiments of the integration of one embodiment of an in vitro model of an in vivo gastrointestinal tract of the present disclosure and a controller.
Figure 10B:
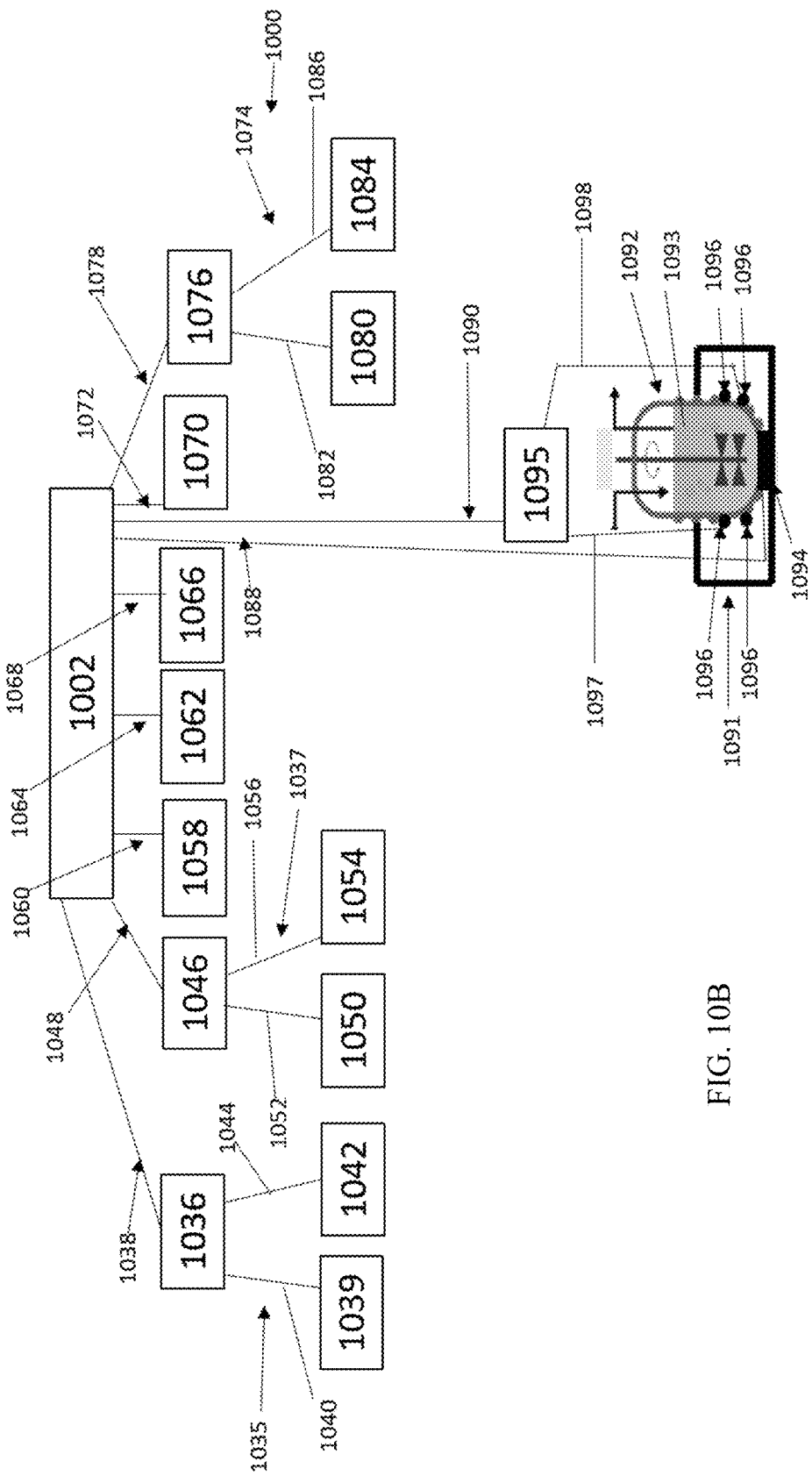
Figure 10C:
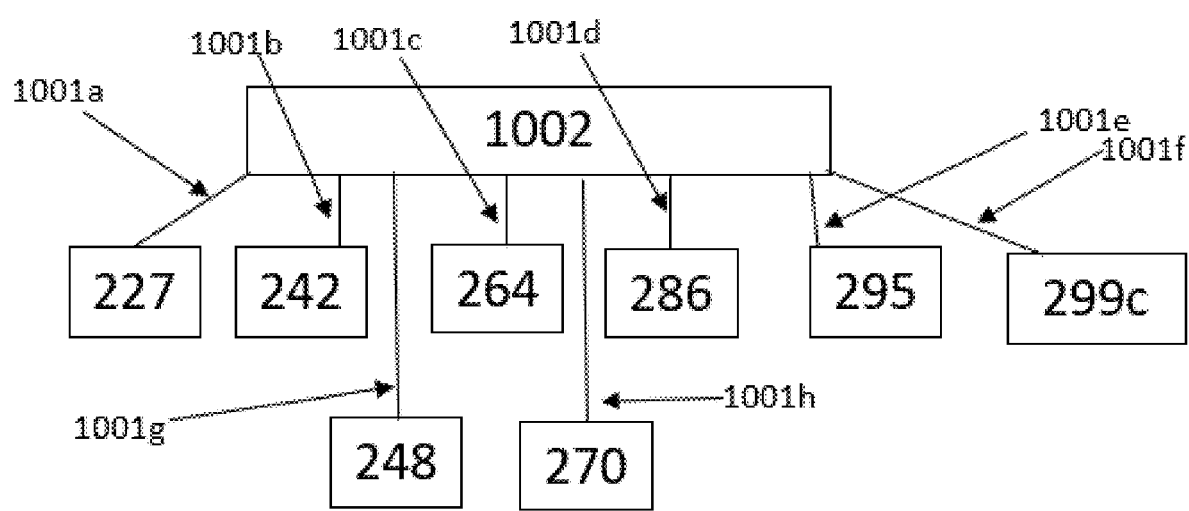

In FIGS. 10A, 10B and 10C, such a control system 1000, such as, for example, the DASgip system is illustrated including a controller 1002. The cables included in the present disclosure can be hardwire (e.g., cables, wires, etc.) and may be used to send data from probes included in embodiments of the present disclosure or send signals to operate motors, pumps or regulators to start/stop and/or regulate the flow therethrough or the speed thereof using hardwired elements and can also include wireless communication means, such as, for example, WIFI or Bluetooth connections. In FIG. 10A, some of the connections of the controller 1002 are illustrated, including the following components illustrated in the embodiment of FIG. 2A for illustrative purposes, the connection to pump 210 via cable 1004, the connection to pump 233 via cable 1006, the connection to pump 231 via cable 1008, the connection to pump 235 via cable 1010, the connection to pump 227 via cable 1012, the connection to pump 232 via cable 1014, the connection to pump 242 via cable 1016, the connection to pump 254 via cable 1018, the connection to pump 264 via cable 1020, the connection to pump 276 via cable 1022, the connection to pump 286 via cable 1024, the connection to pump 288 via cable 1026, the connection to pump 295 via cable 1028, the connection to pump 296 via cable 1030 and the connection to pump 299*d* via cable 1034. The FIG. 2A components and their operation (e.g., on/off and speed (e.g., flow rate)) can be controlled by controller 1002.

In FIG. 10B, System controller 1002 is also connected to other components. As noted above controller 1002 is connected to pump 233 to provide duodenal enzymes from reservoir 214, pump 231 to provide bile acids from reservoir 218 and pump 235 to provide sodium bicarbonate from reservoir 224, all of go into first vessel 212, as shown in FIG. 2A. The other vessels (second vessel 236, third vessel 258, fourth vessel 280, fifth vessel 291 and six vessel 298) each include headplates of the present disclosure described earlier with an acid inlet and base inlet. The first vessel 212 also includes a headplate of the present disclosure described earlier. System 1000 includes an acid supply system 1035 including pump 1036 that is connected to system 1002 via cable 1038 and pumps acid from acid reservoir 1039 via fluid conduit 1040 to acid connector 1042 via fluid conduit 1044. Acid connector 1042 is connected to an acid inlet in the vessel headplate described herein. System 1000 includes a base supply system 1037 including a pump 1046 that is connected to system 1002 via cable 1048 and pumps base from base reservoir 1050 via fluid conduit 1052 to base connector 1054 via fluid conduit 1056. Base connector 1054 is connected to a base inlet in the vessel headplate described herein. There is also a pH probe connector 1058 that is connected via cable 1060 to controller 1002 and is connected to the pH probe of the vessel headplate described herein. When controller 1002 is signaled from pH probe 1058 that the pH of the vessel contents needs to be adjusted, system controller 1002 signals pump 231 or pump 235 for the first vessel 212 or pump 1036 or pump 1046 for the other vessels to add acid or base to the respective vessel depending on whether the pH needs to be raised or lowered. Although only illustrated once, each of the second vessel 236, third vessel 258, fourth vessel 280, fifth vessel 291 and sixth vessel 298 of FIG. 2A has its own dedicated acid supply system 1035 and base supply system 1037, with the possible modification that there is a single acid reservoir and single base reservoir for the entire system and each of the first vessel 212, second vessel 236, third vessel 258, fourth vessel 280, fifth vessel 291 and six vessel 298 of FIG. 2A has its own pH probe connected to controller 1002 as described above.

Also, connected to the respective headplate of each of the first vessel 212, second vessel 236, third vessel 258, fourth vessel 280, fifth vessel 291 and six vessel 298 of FIG. 2A may be a level probe connector 1062 that is connected to the level sensor of the vessel headplate and via cable 1064 to controller 1002, redox probe connector 1066 that is connected to the redox probe of the vessel headplate and via cable 1068 to controller 1002 and temperature probe connector 1070 that is connected to the temperature probe of the vessel headplate and via cable 1072 to controller 1002.

System 1000 includes for each of the first vessel 212, second vessel 236, third vessel 258, fourth vessel 280, fifth vessel 291 and six vessel 298 of FIG. 2A, a gas supply system 1074 including a regulator 1076 that is connected to system 1002 via cable 1078 and regulates the flow of gas from gas reservoir 1080 via fluid connector 1082 to gas connector 1084 via fluid connector 1086, with the possible modification that there is a single gas reservoir for the entire system. The gas supply system is used to provide flowing headspace gas to the vessel, in particular the gas connector 1084 is connected to the gas inlet of the headplate of the vessel. The gas then exits the headspace through the condenser/gas outlet of the headplate.

System 1000 may also include cables 1088 and 1090 that connect controller 1002 to a heating/cooling collar 1091 into which a vessel 1092 is positioned and may be used to adjust the temperature of vessel 1092 and its contents 1093 based on a signal from the temperature probe in the headplate of the vessel (shown in other figures) immersed in the contents of the vessel and connected to controller 1002 as described previously. Any one or all fermentation vessels included in the embodiments of the present disclosure can include a heating/cooling collar that are each separately connected to the controller 1002 that regulates each individually. Cable 1088 is connected to heating element 1094 to heat vessel 1092 and its contents 1093. Cable 1090 can be connected to cooling elements 1096 to cool vessel 1092 and its contents 1093 using cooling coils 1096 (shown in cross-section, but wrapped about the exterior of vessel 1092) and cooling fluid disposed therein supplied via fluid line 1097 and returns the cooling fluid to cooling fluid pump and supply system 1095 via fluid line 1098.

The acid supply system 1035 and base supply system 1037 for embodiments of the present disclosure including, for example, the embodiment of FIG. 2 as others in the present disclosure, include, for example, the DASgip system. The DASgip system include a computing apparatus that works in concert with other components including those of the embodiments of the present disclosure.

In FIG. 10C, some other connections of the controller 1002 are illustrated, including the following components illustrated in the embodiment of FIG. 2A for illustrative purposes, the connection to motor 227 via cable 1001*a*, the connection to motor 242 via cable 1001*b*, the connection to motor 264 via cable 1001*c*, the connection to motor 286 via cable 1001*d*, the connection to motor 295 via cable 1001*e* and the connection to motor 299*c* via cable 1001*f*. The FIG. 2A components and their operation (e.g., on/off and speed (e.g., rotational speed imparted to the agitator to which each is connected)) can be controlled by controller 1002. Controller 1002 can also be used to control the connection to pump 2248 via cable 1001*g* and the connection to pump 270 via cable 1001*h* including to operation of the pumps to start/stop and/or regulate the flow therethrough and to the membrane units described herein.

Embodiments of the present disclosure provide automated fermentation model of the small and large intestine to simulate in vivo functions in an in vitro platform, a system that is fully automated on a commercial platform, a useful head plate design and incorporation of microbial flora specific to the small intestine to enhance physiological relevance of simulated gut and method to establish and maintain community. Other aspects include rationally-designed simplified bacterial communities including sub-set of microbes to explore targeted functional aspects within gut microbiome including, but not limited to, nutrient metabolism, engineered bacteria fate, specific biomarker discovery, enhanced production of novel compounds; and a method for assembly of simplified microbial communities for specific functional studies. Still other aspects include a host:microbiome interface within fermentation model including supported host mucin monolayer for insertion into a fermenter or fermentation process to explore real-time host:bacteria interactions and simulate host interactions with the resident microbiota as well as sustained host component incorporation into colonic models currently does not exist.

Incorporating intestinal microbiota into the small bowel model portion of embodiments of the present disclosure enable a significant increase in physiological relevance of Lower GI Tract Models enabling near final food product formulations to be explored in vitro for efficient digestion thereof with highly realistic changes elicited in the respective microbiomes (small and large) and similar realism engendered to the candidate food products' biotransformation process. In addition, an embodiment could include incorporating the human intestinal tissue (organoid and perhaps tissue engineered) with mucin producing host cells as opposed to mucin-containing beads or without mucin-generating cells, to implement an integrated lower GI tract with both host cells and microbial flora for real-time metabolically-active. Rationally-designed microbial communities for both small and large intestine could also be used in lieu of human-derived complex communities. These simplified communities would have very specific microbial species that would enable very specific tests to be done to access the impact of various food or medical interventions (for example, engineered bacteria) in vitro and enable extrapolation to potential benefits prior to inventing in costly human subject studies. These advantages significantly advance the state of research in the field.

Embodiments of the present disclosure could be used a research tool to screen/down-select various food or medical interventions prior to investing in pilot or full scale human studies/clinical trials and as a result, increase the efficacy of human studies/trials, lower overall development costs and potentially accelerate the transition of these interventions to commercial use. Through incorporation of host component and concept behind simplified community studies, embodiments of the present disclosure could provide improved systematic, functional, cost-effective microbiome analysis that surpasses both current in vitro and animal models. The simplified communities could also be used in any fermentation approach while the host component design can be implemented in other automated fermentation systems. The embodiments of the present disclosure could represent an opportunity to use as a tool to derive knowledge to enhance/optimize Soldier health and performance and for technologies in the microbiome research community.

Soldier gastrointestinal health is impacted by a variety of alterations and stressors not found in the civilian population, such as sustained physical exertion, sleep or nutrient deprivation, and acute/chronic stress. Investigating the impact of these and other conditions on the small and large intestinal microbiomes will inform nutritional and training interventions to improve gut health and Soldier resilience; however, the cost, time and ethical constraints related to human clinical trials limit the breadth of in vivo investigations. Therefore, an in vitro model, such as the embodiments of the present disclosure with improved physiological relevance, enabling cost-effective multiplexed screening of nutrients and conditions prior to clinical trials, is needed to facilitate this process.

Although the dearth of information regarding small bowel microbiota has improved in recent years, information gathering in academia has focused on characterizing the microbiome in a disease state. Incorporating intestinal microbiota into an in vitro small bowel model will enable a significant increase in exploratory studies and significantly advance the state of research in the field. This substantial improvement to the state-of-the-art will directly benefit research regarding Soldier performance and health.

Combination of a small bowel model complements a colonic model by expanding the ability to mimic the function of the human digestive system, in terms of biotransformation of dietary inputs, and enable an accurate representation of the interplay between small and large intestine microbiomes. Development of biofidelic models of the intestinal and gut microbiome also supports an effort related to understanding the influence of Army-centric stressors on gut population dynamics and function, and nutritional intervention strategies to overcome stressors and restore microbiome homeostasis.

Knowledge gained from aspects and embodiments of the present disclosure can impact Soldier performance, by providing analysis of the biotransformation of nutritional components and providing information on performance nutrition studies. In vitro modeling capabilities complement in vivo studies and enable the acquisition of physiologically-relevant knowledge for inclusion in future human clinical studies related to nutritional intervention to overcome Soldier-centric stressors. By enhancing the scope and relevance of clinical studies, the embodiments of the present disclosure will support the development of strategies to enhance Soldier resiliency and maintain a high level of performance under any stressed condition. Furthermore, the embodiments of the present disclosure will advance research leading to simulating the human as a system by incorporating all biofidelic models under development into a single, working model of the human body.

The embodiments of the present disclosure can be utilized to gain knowledge of novel interactions between nutritional components and the small bowel microbiome toward elucidating the role these interactions play in human health. The microbial contribution to host health is difficult to derive in vivo, but a detailed understanding garnered from in vitro simulation can be used to support Soldier GIT health and prevent dysbiosis. It can also serve as a basis for follow-on studies and the next phases of the gut models to enhance in vivo relevance, which is the working goal within all of our in vitro systems. Embodiments of the present disclosure can provide a model to study nutrient metabolism, e.g., mix of bacteria to understand inter-species competition for resistant starch; the fate of engineered bacteria, e.g., monitor persistence and function of engineered probiotic understand increasing levels of microbial competition to mimic gut dynamics and provide feedback for re-design; and enhanced production of novel compounds, e.g. specific community to induce pathways to targeted biomolecule of interest This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. An in vitro model of an in vivo gastrointestinal tract, comprising:
    an in vitro model of an in vivo small intestine including a first plurality of fermentation vessels, comprising:
        an in vitro duodenum model including at least one fermentation vessel having bile acids, sodium bicarbonate and duodenal enzyme disposed therein;

an in vitro jejunum model including at least one fermentation vessel of the first plurality of fermentation vessels having jejunum diluent, growth medium and a of a mixture of aerobic and aerotolerant microorganisms disposed therein; and an in vitro ileum model including at least one fermentation vessel of the first plurality of fermentation vessels having ileum diluent, growth medium and a mock community of a mixture of aerobic and anaerobic microorganisms disposed therein;

an in vitro model of an in vivo large intestine including a second plurality of fermentation vessels, comprising:

an in vitro ascending portion model including at least one fermentation vessel of the second plurality of fermentation vessels having growth medium and a mock community of anerobic microorganisms disposed therein at a pH of about 5.5;

an in vitro transverse portion model including at least one fermentation vessel of the second plurality of fermentation vessels having growth medium and a mock community of anerobic microorganisms disposed therein at a pH of about 6.2;

an in vitro descending portion model including at least one fermentation vessel of the second plurality of fermentation vessels having growth medium and a mock community of anerobic microorganisms disposed therein at a pH of about 6.8; and a first membrane unit in fluid communication with the at least one fermentation vessel of the in vitro jejunum model and a second membrane unit in fluid communication with the at least one fermentation vessel of the in vitro ileum model, the first and second membrane units configured to extract nutrients from the respective contents of the at least one fermentation vessel of the in vitro jejunum model and the at least one fermentation vessel of the in vitro ileum model that pass there through, wherein the first and second plurality of fermentation vessels are in fluid communication.

2. The in vitro model of an in vivo gastrointestinal tract according to claim 1, further including an inlet port of a conduit for the introduction of a mixture of a food product and gastric effluent into one of the plurality of fermentation vessels of the in vitro model of an in vivo small intestine, the port inlet is in fluid communication with the in vitro model of an in vivo small intestine, and the in vitro model of an in vivo small intestine is in fluid communication with the in vitro model of an in vivo large intestine, wherein the in vitro model of an in vivo small intestine is downstream of the inlet port and the in vitro model of an in vivo large intestine is downstream of the in vitro model of an in vivo small intestine.

3. The in vitro model of an in vivo gastrointestinal tract according to claim 1, wherein the in vitro duodenum model further including a source of bile acids, a source of sodium bicarbonate and a source of duodenal enzyme fluidly connected to the at least one fermentation vessel of the in vitro duodenum model.

4. The in vitro model of an in vivo gastrointestinal tract according to claim 1, wherein the mock community of at least one of aerobic, aerotolerant and anaerobic microorganisms disposed in at least one of the at least one fermentation of the in vitro jejunum model and the at least one fermentation of the in vitro ileum model are microbial flora specific to an in vivo small intestine.

5. The in vitro model of an in vivo gastrointestinal tract according to claim 1, further including a mucin producing device to supply mucin to at least one of the plurality of fermentation vessels of the in vitro model of an in vivo large intestine.

6. The in vitro model of an in vivo gastrointestinal tract according to claim 1, wherein the mucin producing device includes an aerobic-host cell scaffold positioned inside the at least one of the plurality of fermentation vessels of the in vitro model of an in vivo large intestine including an enclosure having an interior inside the enclosure, an exterior outside the enclosure, the aerobic host cells growing and disposed in the interior of the enclosure and mucin produced by the aerobic host cells on the exterior of the enclosure.

7. An in vitro model of an in vivo gastrointestinal tract, comprising:

an inlet port of conduit for the introduction of a mixture of a food product and gastric effluent;

an in vitro model of an in vivo small intestine including a first plurality of fermentation vessels, comprising:

an in vitro duodenum model including a first fermentation vessel in fluid communication with the inlet port through a first fluid conduit configured to supply the mixture of a food product and gastric effluent into the first fermentation vessel of the first plurality of fermentation vessels and including a first agitator connected to a first motor configured to move the first agitator to mix contents of the first fermentation vessel, a source of bile acids in fluid communication with the first fermentation vessel through a second fluid conduit including a first pump configured to supply bile acids into the first fermentation vessel, a source of sodium bicarbonate in fluid communication with the first fermentation vessel through a third fluid conduit including a second pump configured to supply sodium bicarbonate into the first fermentation vessel, and a source of duodenal enzymes in fluid communication with the first fermentation vessel through a fourth fluid conduit including a third pump configured to supply duodenal enzymes into the first fermentation vessel;

an in vitro jejunum model including a second fermentation vessel of the first plurality of fermentation vessels in fluid communication with the first fermentation vessel through a fifth fluid conduit including a fourth pump configured to supply a portion of the contents of the first fermentation vessel to the second fermentation vessel, the second fermentation vessel including jejunum diluent, growth medium, and a mock community of aerobic and aerotolerant microorganisms disposed therein and a second agitator connected to a second motor configured to move the second agitator to mix contents of the second fermentation vessel, a first membrane unit in fluid communication with the second fermentation vessel and configured to extract nutrients from the contents of the second fermentation vessel that pass there through and include a first membrane unit inlet, a first membrane unit outlet and a first membrane unit exit port through which the extracted nutrients exit the first membrane unit, a sixth fluid conduit including a fifth pump connected between the second fermentation vessel and the first membrane unit inlet and configured to supply a portion of the contents of the second fermentation vessel to the first membrane unit and a seventh fluid conduit connected between the first membrane unit outlet and the second fermentation vessel and configured to return the contents of the second fermentation vessel that are not extracted by the first membrane unit to the second fermentation vessel; and an in vitro ileum model including
- a third fermentation vessel of the first plurality of fermentation vessels in fluid communication with the second fermentation vessel through an eighth fluid conduit including a sixth pump configured to supply a portion of the contents of the second fermentation vessel to the third fermentation vessel, the third fermentation vessel including ileum diluent, growth medium and a mock community of aerobic and anaerobic microorganisms disposed therein and a third agitator connected to a third motor configured to move the third agitator to mix contents of the third fermentation vessel,
- a second membrane unit in fluid communication with the third vessel and configured to extract nutrients from the contents of the third fermentation vessel that pass there through and include a second membrane unit inlet, a second membrane unit outlet and a second membrane unit exit port through which the extracted nutrients exit the second membrane unit,
- a ninth fluid conduit including a seventh pump connected between the third fermentation vessel and the second membrane unit inlet and configured to supply a portion of the contents of the third fermentation vessel to the second membrane unit and
- a tenth fluid conduit connected between the second membrane unit outlet and the third fermentation vessel and configured to return the contents of the third fermentation vessel that are not extracted by the second membrane unit to the third fermentation vessel; and an in vitro model of an in vivo large intestine including a second plurality of fermentation vessels, comprising:
- an in vitro ascending portion model including a fourth fermentation vessel of the second plurality of fermentation vessels in fluid communication with the third fermentation vessel through an eleventh fluid conduit including an eighth pump configured to supply a portion of the contents of the third fermentation vessel to the fourth fermentation vessel, the fourth fermentation vessel including growth medium and a mock community of anaerobic microorganisms disposed therein at a pH of about 5.5 and a fourth agitator connected to a fourth motor configured to move the fourth agitator to mix contents of the fourth fermentation vessel;
- an in vitro transverse portion model including a fifth fermentation vessel of the second plurality of fermentation vessels in fluid communication with the fourth fermentation vessel through an twelfth fluid conduit including an ninth pump configured to supply a portion of the contents of the fourth fermentation vessel to the fifth fermentation vessel, the fifth fermentation vessel including growth medium and a mock community of anaerobic microorganisms disposed therein at a pH of about 6.2 and a fifth agitator connected to a fifth motor configured to move the fifth agitator to mix contents of the fifth fermentation vessel; and
- an in vitro descending portion model including sixth fermentation vessel of the second plurality of fermentation vessels in fluid communication with the fifth fermentation vessel through an thirteenth fluid conduit including a tenth pump configured to supply a portion of the contents of the fifth fermentation vessel to the sixth fermentation vessel, the sixth fermentation vessel including growth medium and a mock community of anerobic microorganisms disposed therein at a pH of about 6.8 and a sixth agitator connected to a sixth motor configured to move the sixth agitator to mix contents of the sixth fermentation vessel; and a controller configured to:
- selectively at least one of start, stop and regulate the flow there through of each of the fourth pump, sixth pump, eighth pump, ninth pump and tenth pump; and
- selectively at least one of start, stop and regulate the speed of each of the first motor, second motor, third motor, fourth motor, fifth motor and sixth motor.

8. The in vitro model of an in vivo gastrointestinal tract according to claim 7, further including each of the first fermentation vessel, the second fermentation vessel, the third fermentation vessel, the fourth fermentation vessel, the fifth fermentation vessel and the sixth fermentation vessel further including
- a temperature sensor configured to determine a temperature of the contents of the respective fermentation vessel and
- a heating/cooling collar comprising a heating element to heat the respective fermentation vessel and its contents and a cooling element to cool the respective fermentation vessel and its contents; and said controller configured to:
  - receive signals from the temperature sensor indicating the temperature of the contents of each fermentation vessel; and
  - selectively adjust the temperature in each fermentation vessel using the heating/cooling collar of the fermentation vessel.

9. The in vitro model of an in vivo gastrointestinal tract according to claim 7, wherein each of the first fermentation vessel, the second fermentation vessel, the third fermentation vessel, the fourth fermentation vessel, the fifth fermentation vessel and the sixth fermentation vessel further including a pH sensor configured to determine the pH of contents of the respective fermentation vessel and each of the second fermentation vessel, the third fermentation vessel, the fourth fermentation vessel, the fifth fermentation vessel and the sixth fermentation vessel including
- a source of acid in fluid communication with each fermentation vessel and configured to supply acid thereto;
- a source of base in fluid communication with each fermentation vessel configured to supply base thereto; and said controller configured to:
- receive signals from the pH sensor indicating the pH of the contents of each fermentation vessel;
- for the first fermentation vessel, selectively at least one of start, stop and regulate the flow through the first pump to add bile acids to lower the pH of contents of the first fermentation vessel or selectively start or regulate the flow through the second pump to add sodium bicarbonate to raise the pH of contents of the first fermentation vessel;
- for each of the second fermentation vessel, the third fermentation vessel, the fourth fermentation vessel, the fifth fermentation vessel and the sixth fermentation vessel, selectively add acid to lower the pH of contents of each fermentation vessel or selectively add base to raise the pH of contents of the first fermentation vessel each fermentation vessel.

10. The in vitro model of an in vivo gastrointestinal tract according to claim 7, wherein at least one of the in vitro ascending portion model, the in vitro transverse portion model and the in vitro descending portion model further include a third membrane unit configured to extract nutrients from the contents of the respective fermentation vessel that pass there through and include a third membrane unit inlet, a third membrane unit outlet and a third membrane unit exit port through which the extracted nutrients exit the third membrane unit, a thirteenth fluid conduit including a eleventh pump connected between the respective fermentation vessel and the third membrane unit inlet and configured to supply a portion of the contents of the respective fermentation vessel to the third membrane unit and a fourteenth fluid conduit connected between the third membrane unit outlet and the respective fermentation vessel and configured to return the contents of the respective fermentation vessel that are not extracted by the third membrane unit to the respective fermentation vessel.

11. A method of simulating a biotransformation of food product through the human digestive tract using an in vitro model of an in vivo gastrointestinal tract, wherein the in vitro model of an in vivo gastrointestinal tract, comprises:
an inlet port of conduit for the introduction of a mixture of a food product and gastric effluent;
an in vitro model of an in vivo small intestine including a plurality of fermentation vessels, comprising:
an in vitro duodenum model including at least one fermentation vessel of the first plurality of fermentation vessels having bile acids, sodium bicarbonate and duodenal enzyme disposed therein;
an in vitro jejunum model including at least one fermentation vessel of the first plurality of fermentation vessels having jejunum diluent, growth medium and a mock community of aerobic and aerotolerant microorganisms disposed therein; and
an in vitro ileum model including at least one fermentation vessel of the first plurality of fermentation vessels having ileum diluent, growth medium and a mock community of aerobic and anaerobic microorganisms disposed therein;
an in vitro model of an in vivo large intestine including a second plurality of fermentation vessels, comprising:
an in vitro ascending portion model including at least one fermentation vessel of the second plurality of fermentation vessels having growth medium and a mock community of anerobic microorganisms disposed therein at a pH of about 5.5;
an in vitro transverse portion model including at least one fermentation vessel of the second plurality of fermentation vessels having growth medium and a mock community of anerobic microorganisms disposed therein at a pH of about 6.2;
an in vitro descending portion model including at least one fermentation vessel of the second plurality of fermentation vessels having growth medium and a mock community of anerobic microorganisms disposed therein at a pH of about 6.8; and
a first membrane unit in fluid communication with the at least one fermentation vessel of the in vitro jejunum model and a second membrane unit in fluid communication with the at least one fermentation vessel of the in vitro ileum model, the first and second membrane units configured to extract nutrients from the respective contents of the at least one fermentation vessel of the in vitro jejunum model and the at least one fermentation vessel of the in vitro ileum model that pass there through, each of the first and second membrane units including a port to remove the nutrients extracted from the respective first and second membrane units,
the method comprising:
mixing the food product and gastric effluent to form a first mixture;
adding the first mixture to the bile acids, sodium bicarbonate and duodenal enzyme in the at least one fermentation vessel of the in vitro duodenum model including to form a second mixture;
adding a portion of the second mixture to the jejunum diluent, growth medium and mock community of aerobic and aerotolerant microorganisms in the at least one fermentation vessel of the in vitro jejunum model to form a third mixture;
adding a portion of the third mixture to the ileum diluent, growth medium and mock community of aerobic and anaerobic microorganisms in the at least one fermentation vessel of the in vitro ileum model to form a fourth mixture;
adding a portion of the fourth mixture to the growth medium and mock community of anerobic microorganisms in the at least one fermentation vessel of the in vitro ascending portion model to form a fifth mixture;
adding a portion of the fifth mixture to the growth medium and mock community of anerobic microorganisms in the at least one fermentation vessel of the in vitro ascending portion model to form a sixth mixture;
adding a portion of the sixth mixture to the growth medium and mock community of anerobic microorganisms in the at least one fermentation vessel of the in vitro descending portion model to form a seventh mixture; and
removing a portion of the seventh mixture from the at least one fermentation vessel of the in vitro descending portion model, and
collecting at least one sample of one of the first and second membrane units and analyzing the at least one sample.

12. The method according to claim 11, wherein the the in vitro duodenum model further including a source of bile acids, a source of sodium bicarbonate and a source of duodenal enzyme fluidly connected to the at least one fermentation vessel of the in vitro duodenum model.

13. The method according to claim 11, wherein the in vitro model of an in vivo gastrointestinal tract further includes the complex or simplified mock community of at least one of aerobic, aerotolerant and anaerobic microorganisms disposed in at least one of the at least one fermentation of the in vitro jejunum model and the at least one fermentation of the in vitro ileum model are microbial flora specific to an in vivo small intestine.

14. The method according to claim 11, wherein mock community of anaerobic microorganisms disposed in at least one of the at least one fermentation of the in vitro ascending colon model, the at least one fermentation of the in vitro transverse colon model and the at least one fermentation of the in vitro descending colon model are microbial flora specific to an in vivo small intestine.

15. The method according to claim 11, wherein the in vitro model of an in vivo gastrointestinal tract further includes a mucin producing device to supply mucin to at least one of the plurality of fermentation vessels of the in vitro model of an in vivo large intestine.

16. The method according to claim 11, further including taking at least one sample of at least one of the second, third, fourth, fifth and sixth mixtures.

17. The method according to claim 16, further including analyzing the at least one sample of at least one of the second, third, fourth, fifth and sixth mixtures.

18. The method according to claim 11, further including analyzing the portion of the seventh mixture.

* * * * *